US009533037B2

(12) United States Patent
Bonnin et al.

(10) Patent No.: US 9,533,037 B2
(45) Date of Patent: Jan. 3, 2017

(54) METHODS FOR DESIGNING AND PREPARING VACCINES COMPRISING DIRECTED SEQUENCE POLYMER COMPOSITIONS VIA THE DIRECTED EXPANSION OF EPITOPES

(75) Inventors: Dustan Bonnin, Belmont, MA (US); Eric Zanelli, Sudbury, MA (US); Jeff Krieger, Newtonville, MA (US); Thomas Mathers, Boston, MA (US)

(73) Assignee: Declion Holdings LLC, Boxford, MA (US)

( * ) Notice: Subject to any disclaimer, the term of this patent is extended or adjusted under 35 U.S.C. 154(b) by 832 days.

(21) Appl. No.: 12/288,345

(22) Filed: Oct. 16, 2008

(65) Prior Publication Data

US 2011/0129497 A1    Jun. 2, 2011

Related U.S. Application Data

(60) Provisional application No. 60/999,284, filed on Oct. 16, 2007, provisional application No. 61/124,689, filed on Apr. 17, 2008.

(51) Int. Cl.
| A61K 39/145 | (2006.01) |
| A61K 39/12  | (2006.01) |
| C07K 14/005 | (2006.01) |
| A61K 39/00  | (2006.01) |
| C07K 1/04   | (2006.01) |

(52) U.S. Cl.
CPC ............ *A61K 39/145* (2013.01); *A61K 39/12* (2013.01); *C07K 1/047* (2013.01); *C07K 14/005* (2013.01); *A61K 39/00* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| 5,736,142 | A    | 4/1998  | Sette et al. |
| 6,093,396 | A    | 7/2000  | Falorni et al. |
| 6,818,219 | B1   | 11/2004 | Tranchand-Bunel et al. |
| 7,118,874 | B2   | 10/2006 | Torres |
| 8,546,532 | B2 * | 10/2013 | Bonnin ............ C07K 1/047 530/300 |
| 2002/0183484 | A1 | 12/2002 | Torres |
| 2003/0223995 | A1 | 12/2003 | Skurkovich et al. |
| 2006/0045888 | A1 | 3/2006  | Punnonen et al. |
| 2006/0115899 | A1 | 6/2006  | Buckner et al. |
| 2006/0159672 | A1 | 7/2006  | Rasmussen et al. |
| 2008/0146504 | A1 | 6/2008  | Bonnin |
| 2009/0036653 | A1 | 2/2009  | Bonnin |
| 2009/0104216 | A1 | 4/2009  | Torres |
| 2009/0162383 | A1 | 6/2009  | Padlan |
| 2010/0298547 | A1 | 11/2010 | Bonnin |

FOREIGN PATENT DOCUMENTS

| EP | 1 676 859      |    | 7/2006  |
| EP | 1820511        |    | 8/2007  |
| FR | 2677363        | A1 | 12/1992 |
| WO | WO-2005/074579 |    | 8/2005  |
| WO | WO-2005/085323 |    | 9/2005  |
| WO | WO-2005/112972 |    | 12/2005 |
| WO | WO-2006/031727 |    | 3/2006  |
| WO | WO 2006/056027 | A1 | 6/2006  |
| WO | WO 2006/128294 |    | 12/2006 |
| WO | WO-2007/120834 |    | 10/2007 |
| WO | WO-2008/033105 |    | 3/2008  |
| WO | WO-2008/049974 |    | 5/2008  |
| WO | WO-2009/023047 |    | 2/2009  |
| WO | WO-2009/089121 |    | 7/2009  |
| WO | WO-2009/103105 |    | 8/2009  |

OTHER PUBLICATIONS

Muller et al., Anti-influenza response achieved by immunization with a synthetic conjugate, 1982, PNAS, vol. 79, pp. 569-573.*
Brown et al., Conservation of Determinants for Class II-Restricted T Cells within Site E of Influenza Virus Hemagglutinin and Factors Influencing Their Expression, Journal of Virology, 1993, vol. 67, No. 5, pp. 2887-2893.*
Alexander, J. et al., "Linear PADRE T Helper Epitope and Carbohydrate B Cell Epitope Conjugates Induce Specific High Titer IgG Antibody Responses", The Journal of Immunology, 200, 164: 1625-1633.
Berzofsky, J. et al., "Progress on new vaccine strategies against chronic viral infections", J. Clin. Invest. 114:450-462 (2004).
Berzofsky, J. et al., "Progress on new vaccine strategies for the immunotherapy and prevention of cancer", J. Clin. Invest. 113:1515-1525 (2004).
Celis, E., "Getting peptide vaccines to work: just a matter of quality control", J. Clin. Invest. 110:1765-1768 (2002).
Chen, J. et al., "Structural and kinetic basis for heightened immunogenicity of T cell vaccines", JEM, 201:1243-1255 (2005).
Cornberg, M. et al., "Narrowed TCR repertoire and viral escape as a consequence of heterologous immunity", J. Clin. Invest. 116:1443-1456 (2006).
Daniels, R.S. et al., "The receptor-binding and membrane-fusion properties of influenza virus variants selected using anti-haemagglutinin monoclonal antibodies", The EMBO Journal, 6:1459-1465 (1987).
Frenkel, D. et al., "Nasal vaccination with a proteosome-based adjuvant and glatiramer acetate clears β-amyloid in a mouse model of Alzheimer disease", J. Clin. Invest. 115:2423-2433 (2005).

(Continued)

*Primary Examiner* — Benjamin P Blumel
(74) *Attorney, Agent, or Firm* — Ropes & Gray LLP

(57) ABSTRACT

The instant invention comprises a process of preparing a composition comprising directed sequence polymer (DSP) mixtures that act as epitopes and useful as vaccines, such DSP synthesized according to a set of rules regarding the identity and the frequency of occurrence of amino acids that substitute a base or native amino acid of a known epitope. The resulting composition is a mixture of related peptides for therapeutic use as a vaccine, preferably for infectious agents that are immune evasive.

17 Claims, 11 Drawing Sheets

(56) References Cited

OTHER PUBLICATIONS

Hoffmann, E. et al., "Role of specific hemagglutinin amino acids in the immunogenicity and protection of H5N1 influenza virus vaccines", PNAS, 102:12915-12920 (2005).

June, C., "Principles of adoptive T cell cancer therapy", J. Clin. Invest. 117:1204-1212 (2007).

Kashyap, A. et al., "Combinatorial antibody libraries from survivors of the Turkish H5N1 avian influenza outbreak reveal virus neutralization strategies", PNAS, 105:5986-5991 (2008).

Kaverin, N. et al., "Structure of antigenic sites on the haemagglutinin molecule of H5 avian influenza virus and phenotypic variation of escape mutants", J. of General Virol., 83:2497-2505 (2002).

Mayordomo, J. et al., "Therapy of Murine Tumors with p53 Wild-type and Mutant Sequence Peptide-based Vaccines", J. Exp. Med., 183:1357-1365 (1996).

Melchionda, F. et al., "Adjuvant IL-7 or IL-15 overcomes immunodominance and improves survival of the CD8+ memory cell pool", J. Clin. Invest., 115:1177-1187 (2005).

Olszewska, W., et al., "Nasal delivery of epitope based vaccines", Advanced Drug Delivery Reviews, 51:161-171 (2001).

Rosenthal, K. et al., "Vaccines: All Things Considered", Clin. and Vaccine Immunol., 821-829 (2006).

Speiser, D. et al., "Rapid and strong human CD8+ T cell responses to vaccination with peptide, IFA, and CpG oligodeoxynucleotide 7909", J. Clin. Invest. 115:739-746 (2005).

Stevens, J. et al., "Structure and Receptor Specificity of the Hamagglutinin from an H5N1 Influenza Virus", Science, 312:404-409 (2006).

Suzuki, Y. et al., "Sialic Acid Species as a Determinant of the Host Range of Influenza A Viruses", J. of Virol., 74:11825-11831 (2000).

Tam, J. et al., "Incorporation of T and B Epitopes of the Circumsporozoite Protein in a Chemically Defined Synthetic Vaccine Against Malaria", J. Exp. Med., 171:299-306 (1990).

Tabor, E., "Infections by Hepatitis B Surface Antigen Gene Mutants in Europe and North America", J. Med. Virol., 78:S43-S47 (2006).

Yamada, S. et al., "Haemagglutinin mutations responsible for the binding of H5N1 influenza A viruses to human-type receptors", Nature, 444:378-382 (2006).

Estaquier, J., et al., "Combinatorial Peptide Library as an Immunogen," Methods in Molecular Biology, 87:281-296 (1998).

Estaquier, Jerome, et al., "A Combinatorial Peptide Library Around Variation of the Human Immunodeficiency Virus (HIV-1) V3 Domain Leads to Distinct T Helper Cell Responses," Journal of Peptide Science, 2:165-175 (1996).

Gras-Masse, H., et al., "Confronting the degeneracy of convergent combinatorial immunogens, or 'mixotopes', with the specificity of recognition of the target sequences," Vaccine, 15(14):1568-1578 (1997).

Gras-Masse, Helene, et al., "Convergent peptide libraries, or mixotopes, to elicit or to identify specific immune responses," Immunology, 11:223-228 (1999).

Tranchand-Bunel D, et al., "Evaluation of an Epstein-Barr Virus (EBV) Immunoglobulin M Enzyme-Linked Immunosorbent Assay Using a Synthetic Convergent Peptide Library, or Mixotope, for Diagnosis of Primary EBV Infection," J Clin Microbiol., 37(7):2366-2368 (Jul. 1999).

Anderson, "Overcoming original (antigenic) sin" Clinical Immunology, Academic Press, US, vol. 101, No. 2, pp. 152-157 (2001).

Chianese-Bullock, K., et al. "MAGE-A1, MAGE-A10-, and gp100-Derived Peptides are Immunogenic When Combined with Granulocyte-Macrophage Colony-Stimulating Factor and Montamide IS-51 Adjuvant and Administered as Part of a Multipeptide Vaccine for Melanoma", The Journal of Immunology, 174, 3080-3086 (2005).

De Koster, H. et al., "Definition of agonists and design of antagonists for alloreactive T cell clones using synthetic peptide libraries", International Immunology, vol. 11, No. 4, 585-591 (1999).

Glich et al., "Polyclonal Anit-PrP Auto-antibodies Induced with Dimeric PrP Interfere Efficiently with $PrP^{SC}$ Propagation in Prion-infected Cells" The Journal of Biological Chemistry 278(20): 18524-18531 (2003).

Guevara-Patino, J. et al. "Optimization of a self antigen for presentation of multiple epitopes in cancer immunity", J. Clin. Invest. 116:1382-1390, (2006).

Harmeyer et al., "Synthetic peptide vaccines yield monoclonal antibodies to cellular and pathological prion proteins of ruminants" Journal of General Virology 79: 937-945 (1998).

Hernandez, J., et al. "Antigenicity and immunogenicity of peptide analogues of a low affinity peptide of the human telomerase reverse trascriptase tumor antigen", Eur. J. Immunol. 34:2331-2341, (2004).

Hoogenboom, H., "Selecting and screening recombinant antibody libraries", Nature Biotechnology, vol. 23, No. 9 1105-1116 2005.

Hust, M., et al., "Mating antibody phage display with proteomics", TRENDS in Biotechnology, vol. 22 No. 1, 8-14 2004.

Kim, et al., "Persistence of Immune Responses to Altered and Native Myelin Antigens in Patients with Multiple Sclerosis Treated with Altered Peptide Ligand", Clinical Immunology, 104:2, 105-114 (2002).

Kirsch, M., et al., "Parameters affecting the display of antibodies on phage", Journal of Immunological Methods, 301,173-185, 2005.

Knappik, A., et al., "FullySynthetic Human Combinatorial Antibody Libraries (HuCAL) Based on Modular Consensus Frameworks and CDRs Randomized with Trinucleotides", J. Mol. Biol. 296 57-86, 2000.

Konthur, Z., et al., "Perspectives for systematic in vitro antibody generation", Gene, 364, 19-29,2005.

Laurie et al., "CD4+ T cells from Copolymer-1 immunized mice protect dopaminergic neurons in the 1-methyl-4-phenyl-1,2,3,6-tetrahydropyridine model of Parkinson's disease", Journal of Neuroimmunology, 183:60-8 (2007).

Loiseau, P., et al., "HLA class II polymorphism contributes to specify desmoglein derived peptides in pemphigus vulgaris and pemphigus floiaceus", Journal of Autoimmunity, 15, 67-73 (2000).

Lustgarten et al: "Identification of cross-reactive pepides using combinatioral libraries circumvents tolerance against Her-21neu-immunodominant epitope", Journal of Immunology, vol. 176, No. 3, 1796-1805 (2006).

Maynard, J., et al., "Structure of an Autoimmune T Cell Receptor Complexed with Class II Peptide-MHC: Insights into MHC Bias and Antigen Specificity", Immunity, vol. 22, 81-92 (2005).

Morrison K L et al: "Combinatorial alanine-scanning" Current Opinion in Chemical Biology, Current Biology Ltd, London, GB, vol. 5, No. 3, Jun. 1, 2001 (Jun. 1, 2001), pp. 302-307.

O'Sullivan, D., et al., "On the interaction of promiscuous antigenic peptides with different dr alleles", The Journal of Immunology, vol. 147, No. 8, 2663-2669, (1991).

Osbourn, J., et al., "Current methods for the generation of human antibodies for the treatment of autoimmune diseases", DDT, vol. 8, No. 18,845-851 2003.

Pankiewicz, et al "Clearance and prevention of prion infection in cell culture by anti-PrP antibodies" Eur J Neurosci. May 2006; 23(10): 2635-2647.

Pinchuk, P., et al., "Antigenicity of polypeptides (poly alpha amino acids )", Microbiology Department, New Jersey College of Medicine and Dentistry, 673-679 (1965).

Pinilla, C., et al., "Advances in the use of synthetic combinatorial chemistry: Mixture-based libraries", Nature Medicine, vol. 9, No. 1, , pp. 118-126, (2003).

Pons J et al: "Energetic analysis of an antigen/antibody interface: alanine scanning mutagenesis and double mutant cycles on the HyHEL-10/lysozyme interaction." Protein Science o A Publication of the Protein Society May 1999, vol. 8, No. 5, May 1999 (May 1999), pp. 958-968.

Sakurai, Y. et al., "Analog Peptides of type II collagen can suppress arthritis in HLA-DR4 (DRB1*0401) transgenic mice", Arthritis Research & Therapy, 8:R150, (2006).

Tsai, S.-J., "Glatiramer acetate could be a potential therapeutic agent for Parkinson's disease through its neuroprotectiev and anti-inflammatory effects", Medical Hypotheses, 69:1219-21 (2007).

(56) References Cited

OTHER PUBLICATIONS

Wilson, D. et al, "Specificity and degeneracy of T cells", Molecular Immunology 40:1047-1055, (2004).
Anderson, D., et al., "Overcoming Original (Antigenic) Sin", Clinical Immunology, vol. 101, No. 2, pp. 152-157, 2001.
Bianchi, E., et al., "Universal Influenza B Vaccine Based on the Maturational Cleavage Site of the Hemagglutinin Precursor", Journal of Virology, vol. 79, No. 12, pp. 7380-7388, Jun. 2005.
Carlos, M., et al., "Immunogenicity of a Vaccine Preparation Representing the Variable Regions of the HIV Type 1 Envelope Glycoprotein", Aids Research and Human Retroviruses, vol. 16, No. 2, pp. 153-161, 2000.
Meyer, D., et al., "Hypervariable Epitope Constructs Representing Variability in Envelope Glycoprotein of SIV Induce a Broad Humoral Immune Response in Rabbits and Rhesus Macaques", Aids Research and Human Retroviruses, vol. 14, No. 9, pp. 751-760, 1998.
Meyer, D., et al., "Induction of Cytotoxic and Helper T Cell Responses by Modified Simian Immunodeficiency Virus Hypervariable Epitope Constructs", Viral Immunology, vol. 12, No. 2, pp. 117-129, 1999.
Pantophlet, R., et al., "Improved design of an antigen with enhanced specificity for the broadly HIV-neutralizing antibody b12", Protein Engineering, Design & Selection, vol. 17, No. 10, pp. 749-758, 2004.
International Search Report dated Mar. 18, 2009 in corresponding International Application No. PCT/US2008/011871.
Jardetzky et al "Peptide binding to HLA-DR1: a peptide with most residues substituted to alanine retains MJC binding," The EMBO Journal, 9(6):1797-1803 (1990).
Liu et al., "High epitope density in a single protein molecule significantly enhances antigenicity as well as immunogenicity: a novel strategy for modern vaccine development and a preliminary investigation about B cell discrimination of monomeric proteins," European Journal of Immunology, 35(2):505-514 (2005).

* cited by examiner

Directed Sequence Polymer Creation

Steps for Creation of Directed Sequence Polymer

Figure 4

Preferred Defined Substitutive Rules for Directed Expansion of Epitope Permeability

Amino Acid groupings used for exchanging amino acids during the creation of rules for the solid phase synthesis of DSP. Amino Acids grouped together are interchangeable.

| | a | b | c | d |
|---|---|---|---|---|
| I | | R,H | | K |
| II | | W | | |
| III | | F,Y | | |
| IV | | | V,I,L,M | |
| V | | | C | |
| VI | T,S,G,P | | | |
| VII | | | | E,D,Q,N |
| Alanine | Alanine can be substituted for any amino acid | | | |

Figure 5

Generic Rule Structure and Ranges of Substitutions of DSP Synthesis

| | Sequence of amino acids to be synthesized (Amino Acid Sequence Synthesis Block $y_N$) | | | | | | Input Ratio |
|---|---|---|---|---|---|---|---|
| Base (a) | $x_1$ | $x_2$ | $x_3$ | $x_4$ | $x_5$ | $x_N$ | a = 0.0 - 80 |
| 1° Change (b)_ | $1°x_1$ | $1°x_2$ | $1°x_3$ | $1°x_4$ | $1°x_5$ | $1°x_N$ | b = 0.0 - 80 |
| 2° Change (c) | $2°x_1$ | $2°x_2$ | $2°x_3$ | $2°x_4$ | $2°x_5$ | $2°x_N$ | c = 0.0 - 80 |
| 3° Change (d) | $3°x_1$ | $3°x_2$ | $3°x_3$ | $3°x_4$ | $3°x_5$ | $3°x_N$ | d = 0.0 - 80 |
| Alanine (e) | Ala | Ala | Ala | Ala | Ala | Ala | e = 20 - 100 |

Full Length Order of DSP

| | N-terminal Modifier | Amino Acid Sequence Synthesis Block | | | | | | C-terminal Modifier |
|---|---|---|---|---|---|---|---|---|
| DSP | MN | $y_1$ | $y_2$ | $y_3$ | $y_4$ | $y_5$ | $y_n$ | MC |

Figure 6

Example of mock-source peptide DSP Synthesis Rules

Rules of Defined Amino Acid Incorporation

| Input Ratios | y1 Amino Acid (% of total at position) | | | | | Input Ratios | y2 Amino Acid (% of total at position) | | | | |
|---|---|---|---|---|---|---|---|---|---|---|---|
| a(35) | T(35%) | H(45%) | M(40%) | C(50%) | E(35%) | a(4) | P(4%) | W(34%) | K(34%) | N(24%) | A(34%) |
| b(5) | S(5%) | R(5%) | V(5%) | | D(5%) | b(10) | T(10%) | | | Q(10%) | |
| c(5) | G(5%) | | I(5%) | | Q(5%) | c(10) | S(10%) | | | | |
| d(5) | P(5%) | | | | N(5%) | d(10) | G(10%) | | | | |
| e(50) | A(50%) | A(50%) | A(50%) | A(50%) | A(50%) | e(66) | A(66%) | A(66%) | A(66%) | A(66%) | A(66%) |

Rules of Synthesis Block Combination and Modification

| N-Terminal Modification | Body of a Directed Epitope Peptide Mixture or Directed Sequence Polymer (DSP) | | | | | | | C-Terminal Modification |
|---|---|---|---|---|---|---|---|---|
| | y1 | y1 | y2 | y2 | y1 | y1 | y2 | y2

Figure 7A

HA Egret Egypt 1162 Namru 3 06 (H5N1)
Top

Hyper-variable Regions

Inward Facing

Figure 7B

HA Egret Egypt 1162 Namru 3 06 (H5N1)

Looking Inside Out

Top

Hyper-variable Regions

Figure 7C

DEEP-Flu Targeting
HA Egret Egypt 1162 Namru 3 06 (H5N1)

Figure 7D

DEEP-Flu Design

| Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| Amino Acids | | | | | | | | | | | | | | | | | | | | | | | | | |
| 1 | C | T | I | P | K | S | S | W | S | D | H | E | A | S | S | G | V | S | S | A | C | P | Y | Q | G |
| 2 | | | | | | | | | P | S | | D | | | L | | | A | | | | | | H | |
| 3 | | | | | | | | | | N | | | | | | | | | | | | | | N | |
| 4 | | | | | | | | | | | | | | | | | | | | | | | | L | |
| 5 | | | | | | | | | | | | | | | | | | | | | | | | | |
| 6 | | | | | | | | | | | | | | | | | | | | | | | | | |
| 7 | | A | A | A | A | A | A | A | A | A | A | | A | A | | | | | | A | | | | A | A |
| Percentage | | | | | | | | | | | | | | | | | | | | | | | | | |
| 1 | 100 | 70 | 70 | 70 | 70 | 70 | 70 | 70 | 70 | 40 | 90 | 65 | 100 | 90 | 65 | 100 | 100 | 100 | 100 | 100 | | 100 | 100 | 40 | 90 |
| 2 | | | | | | | | | 20 | 20 | | 25 | | | 25 | | | | | | | | | 30 | |
| 3 | | | | | | | | | | 30 | | | | | | | | | | | | | | 20 | |
| 4 | | | | | | | | | | | | | | | | | | | | | | | | | |
| 5 | | | | | | | | | | | | | | | | | | | | | | | | | |
| 6 | | | | | | | | | | | | | | | | | | | | | | | | | |
| 7 | | 30 | 30 | 30 | 30 | 30 | 30 | 30 | 10 | 10 | 10 | 10 | | 10 | 10 | | | | | 100 | | | | 10 | 10 |
| TOTAL | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

| Position | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 |
|---|---|---|---|---|---|---|---|---|---|---|---|---|---|---|---|---|---|---|---|---|---|---|---|---|---|---|
| Amino Acids | | | | | | | | | | | | | | | | | | | | | | | | | | |
| 1 | R | S | S | F | F | R | N | V | V | W | L | I | K | K | D | N | A | Y | P | T | I | K | R | S | Y | C |
| 2 | K | P | | Y | | | | | | | | T | T | R | N | S | T | | | | | K | | | | |
| 3 | S | | | | | | | | | | | V | E | | D | S | | | | | | | | | | |
| 4 | V | | | | | | | | | | | | | | | | | | | | | | | | | |
| 5 | T | | | | | | | | | | | | | | | | | | | | | | | | | |
| 6 | G | | | | | | | | | | | | | | | | | | | | | | | | | |
| 7 | A | A | | | | | | | | | | A | A | A | A | A | | | | | | | | | | |
| Percentage | | | | | | | | | | | | | | | | | | | | | | | | | | |
| 1 | 20 | 45 | 100 | 100 | 100 | 100 | 100 | 100 | 100 | 100 | 100 | 70 | 70 | 80 | 45 | 40 | 40 | 100 | 100 | 100 | 100 | 60 | 100 | 100 | 100 | 100 |
| 2 | 15 | 45 | | | | | | | | | | 10 | 10 | 10 | 45 | 40 | 40 | | | | | 40 | | | | |
| 3 | 15 | | | | | | | | | | | 10 | 10 | | | 10 | 20 | | | | | | | | | |
| 4 | 15 | | | | | | | | | | | | | | | | | | | | | | | | | |
| 5 | 15 | | | | | | | | | | | | | | | | | | | | | | | | | |
| 6 | 10 | | | | | | | | | | | | | | | | | | | | | | | | | |
| 7 | 10 | 10 | | | | | | | | | | 10 | 10 | 10 | 10 | 10 | | | | | | | | | | |
| TOTAL | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |

Figure 7E

DEEP-Flu Targeting
HA Egret Egypt 1162 Namru 3 06 (H5N1)

METHODS FOR DESIGNING AND PREPARING VACCINES COMPRISING DIRECTED SEQUENCE POLYMER COMPOSITIONS VIA THE DIRECTED EXPANSION OF EPITOPES

RELATED APPLICATIONS

This application claims the benefit of U.S. Provisional Application 60/999,284 filed Oct. 16, 2007, and U.S. Provisional Application 61/124,689, filed Apr. 17, 2008.

FIELD OF INVENTION

This application provides methods of making improved compositions of peptide vaccines and provides methods of overcoming attenuated and inadequate immune responses associated with immune evasion.

BACKGROUND OF THE INVENTION

The infection of a host by an infectious pathogen is a complex event comprising a series of coordinated events in which the pathogen attempts to evade both the host's innate and adaptive immune systems. In their attempts to replicate and survive, the invading pathogens cause damage to the host. The destruction generally takes the form of cell death, either from pathogen entry into the cell or from endo/exo-toxins produced by the pathogen, as well as the induction of host cellular responses that have the ability to cause further tissue damage, scarring or hypersensitivity. Although between 1938 and 1952, the decline in infectious disease-related mortalities decreased 8.2% per year (Armstrong, G L et al., *JAMA* 1999, 281:61-6), the death rates due to infectious disease have been increasing since the 1980s. A study performed at the National Center for Infectious Diseases demonstrated that the death rate due to infectious diseases as the underlying cause of death increased 58% from 1980 to 1992. In 1992, 64 of every 1,000 deaths were attributable to infectious disease (Pinner, R W et al., *JAMA* 1996, 275:3).

The mechanisms of infectious diseases comprise two distinct but interconnected aspects: (1) the various organisms attempting to invade a host, each different class of infectious agents having distinct means by which they attempt to evade the host's immune system, and (2) the host's immune response to the invading pathogen. Humans have warded off infectious diseases in both of these aspects, in the first aspect, by preventing the access of infectious agents (e.g. by sanitary habits) and in the second aspect, by assisting and boosting the immune system by, for example, vaccination.

The Fight Against Infectious Disease

Immunization programs in the effort to control infectious diseases, such as small-pox, polio, measles, mumps, rubella, influenza caused by *Haemophilus influenza* (flu), pertussis, tetanus, and diphtheria, used centuries old technology to safely create an immune response in a host prior to pathogenic infection by the live organism. These vaccination protocols called for the introduction to the host of an inactive or very weak form of the actual pathogen, and in so doing an active immune response was created.

To make vaccination more effective, advances in eliciting stronger immune responses have been made with the development of antigen/epitope non-specific treatments that boost immune activity, such as the adjuvant alum (see *Vaccine Adjuvants and Delivery Systems*, edited by Manmohan Singh 2007 Wiley & Sons ISBN: 978-0-471-73907-4, incorporated by reference herein, for an extensive review of vaccine adjuvants), as well as development of immunogens based on the understanding of the genetic basis of these pathogens (GenBank, a database managed by the National Center for Biotechnology Information, now has over 85 billion base pairs in its database. Searching based on pathogen is widely used (http://www.ncbi.nlm.nih.gov/Genbank/). The latter has opened up the possibility of utilizing discrete sequences of proteins derived from the pathogen as immunizing agents in the context of cell-mediated (T cell via MHC class I and/or II), but not humoral (Bcell/antibody-mediated immunity). These peptide-based vaccines are specific to epitopes (also called antigenic determinants) that are the precise moieties within antigenic materials to interact with immune system components, intended to boost immune reactivity, and are administered using methods designed to excite immune function. One major limitation of the epitope/peptide-based approach is the variability with which the human MHC class I and II receptors bind the peptides.

While improvements to the techniques have been made in the form of differing types of inactivation of pathogen or in the use of adjuvants to enhance immunogenicity, there remain infectious diseases that are generally refractory to traditional vaccine therapies. In the context of influenza vaccines specific for a particular strain of the virus, clinical efficacy rates range near 40% when there is not a match with the circulating strain (Ben-Yedidia, T and Arnon, R, *Expert Rev. Vaccine* 2007, 6:939-948).

A need remains in the development of vaccines that can handle the infectious agents such as human immunodeficiency virus (HIV), cytomegalovirus, and severe acute respiratory syndrome coronavirus, as well as bacteria such as *Pseudomonas aeruginosa, Neisseria gonorrhea*, or *Mycobacterium tuberculosis* or parasitic diseases such as malaria or hookworm disease. In the context of influenza, the current licensed vaccines are produced in eggs, and make use of half-century old technology (Ben-Yedidia 2007, above).

These infectious agents, bacteria, and parasitic diseases are harder to treat using the inactive pathogen vaccine approach because of the organism's ability to evade host detection. The HIV or the flu virus has the ability to alter its immune profile multiple times in the amount of time less than a calendar year, progressively marginalizing the effectiveness of immunity gained by previous infection and/or even the most recently created vaccine.

In particular, flu viruses, which can easily spread widely and ubiquitously throughout the world, have a large adverse effect on the human population, affecting 10-20% of the total world-wide population (Ben-Yedidia 2007, above). Flu viruses are categorized into three types, A, B, and C. Influenza C rarely infects humans, but influenza A viruses infect various species and B viruses are specific to humans. A and B can be highly virulent. The human immune system attacks flu viruses by targeting their surface proteins hemagglutinin (HA) and neuraminidase (NA). As such, subtypes of flu viruses are categorized as combination of HA type and NA type. HA is a tri-valent viral glycoprotein with two subunits H1 and H2. The virus uses the H1 portion to gain entry to host cells by binding to α2-6 linked sialosides (human), or 2-3 linked sialosides (avian) (Stevens, J et al., *J. Mol. Biol.* 2008, 381:1382-1394). The secondary and tertiary structures of HA have been solved (Wilson, I A et al., *Nature* 1981, 289:366-73). Currently there are 15 known subtypes of HA and 9 known subtypes of NA.

The difficulty for the human body to effectively counter influenza infection lies in the fact that the HA protein mutates quickly, allowing the viruses to evade the host organism's immune system. The average rate of amino acid substitutions is 3.6 per year (Smith, D J et al., *Science* 2004, 305:371-6). Once a mutation occurs in a given epitope region of influenza HA, a second mutation does not immediately occur in that epitope region resulting in a linear profile of temporal appearance of mutation sequence clusters in HA (Plotkin, J B et al., *Proc. Nat. Acad. Sci. USA* 2002, 99:6263-68). The H1 subunit of HA has been shown to have five main antigenic epitopes. In these regions the amount of mutation is significantly higher than in other regions of the protein.

It is important to understand the metes and bounds of the immunity induced in a host by immunization with a single strain of influenza; how said host responds to another strain dictates the selection of the next vaccine strain. The mutations in the influenza HA protein are subdivided into two groups, antigenic drift and antigenic shift. Antigenic drift is a phenomenon where the protein sequence of HA changes, resulting in immune evasion and improved ability of the virus to enter and replicate in a host cell. Drift measurement metrics have evolved and include the Hamming and Miyata metrics (Miyata, T et al., *J. Mol. Evol.* 1979, 12:219-36; Henikoff, S et al., *Proc. Nat. Acad. Sci. USA* 1992, 89:10915-19). Antigenic drift causes the seasonal flu surge that is usually not lethal to otherwise healthy people with normal immune system, but it still affects 10-20% of the world's human population, with up to 5 million cases of serious illness and half million deaths, according to the World Health Organization (WHO). Using the Hamming metric, investigators have suggested that no viral cluster (drifted sequences) has members that last longer than seven years, due to new dominant clusters that replace one another on average every 2-5 years. Other investigators have characterized the inter-pandemic evolution of influenza as intervals of immunologically neutral sequence evolution without significant antigenic alteration. During this time of stasis, there is a slow extinction of coexisting virus lineages that is contrasted with rapid and dramatic excess of amino acid replacements in the variable, or epitopic regions of HA, resulting in the ascension of the new dominant strain at the expense of the earlier variants (Wolf Y I et al., *Biology Direct* 2006, 34:1-19). These investigators determined that in periods of slow extinction (drift), the ratio of the number of amino acid replacements in the variable, or epitopic regions to the non-variable regions was 9:8, whereas periods of rapid extinction (shift) saw a ratio of 23:1 (Wolf, 2006, above). Thus one means to define a cluster of variants is those currently existing strains that have a ratio smaller than 9:8 of amino acid changes between epitopic and non-epitopic regions.

Antigenic shift, on the other hand, is a major change, requiring four or more amino acid changes across two or more antigenic sites (Plotkin, 2002 above). Such antigenic shift causes an increase in pathology and mortality in humans because of their immunological naiveté to the new strain. In the past, the fast expansions of Spanish flu or Hong Kong flu were deadly. Recently a threat of the H5N1 strain, the "bird flu" more fully described below, turning into a human pandemic strain is emerging.

The modern world has combated influenza epidemics by attempting to predict the next prevalent viral subtype and vaccinating people against it. In 1952, the WHO established the Influenza Program to assist fight against influenza epidemic, and coordinates a network of over 100 influenza surveillance centers all over the world. The centers characterize the antigenic properties of the isolated viruses using a test known as the hemagglutination inhibition (HI) assay, which measures the ability of the virus to agglutinate red blood cells, and the capability of antisera against related strains to inhibit such agglutination. The results of the HI assay is measured in units called antigenic distances, each of which unit corresponding to a twofold dilution of anti-sera in the assay (Smith, 2004, above). Thus a subsequent means to identify a cluster of variants is those currently existing strains having less than a twofold dilution of anti-sera in the HI assay.

In the United States, the Vaccines and Related Biological Products Advisory Committee of the Division of Viral Products ("the Vaccines Committee") at the Center for Biologics Evaluation and Research (CBER) of the Food and Drug Administration defines the most relevant strains for the production of vaccines using the HI assay. When the antigenic distance is greater than two, the Vaccines Committee will update the variant for the upcoming season (Smith, 2004, above). For the Northern Hemisphere's 2008-9 season, for example, the Vaccines Committee recommended H1N1 A/Brisbane/59/2007 and H3N2 A/Brisbane/10/2007 for Influenza A and B/Florida/4/2006 for Influenza B for the seasonal production of licensed vaccines (inactivated or attenuated viruses).

The choice of the Vaccines Committee of which is the appropriate strain for the upcoming season's vaccine production and distribution is based in large part on antigenicity. Quantitative measurements of antigenic data include numerical taxonomy or its equivalent (Papaud, A, Poisson A, *J Mar Res* 1986, 44:385; Mecking S, Warner J, *Geophys Res* 1999, 104:11087), the method of Lapedes and Farber (Wallace D W R, Ocean Circulation and Climate Academic Press San Diego, Calif. 2001 pp 489-521) which uses ordinal multidimensional scaling in the interpretation of binding data so that an antigenic map, or the distance between an antigen and antiserum can be visualized. A refinement of the Lapedes and Farber method (Smith D J, 2004, above; Sabine C L et al., *Global Biogeochem Cycles* 16:1083, 2002) positions/overlays the antigens and the antisera on a map.

An alternate approach of defining clusters is differentiation by the organization of genetic (DNA) data into phylogenetic trees. The international surveillance programs are responsible for the majority of the sequencing performed in order to identify serologically novel influenza strains (Layne S P, *Emerg. Infect. Dis.* 12:562-68, 2006). Investigators have reported that the meaningful antigenic changes that occurred in an H3N2 subtype influenza virus during the period between 1983 ad 1997 were found predominantly in the internal and not external branches of the tree (Bush, R M et al. *Mol Biol Evol* 1999, 16:1457-65). Thus a further subsequent means to identify a cluster of variants is the branching organization of those currently existing strains obtained using genetic data.

There are various types of vaccines available for human use: DNA-based, cellular, live pathogen, attenuated or inactivated pathogen-based, recombinant protein and peptides. There are currently five inactivated seasonal vaccines for human use (Fluzone®, Fluvirin®, Fluarix®, FluLaval®, and Afluria®), and one live attenuated (FluMist®). Peptide based vaccines can be either recombinant or synthetic. Since 1993 there have been over 1,000 peptide based vaccines in pre-clinical research, over 100 in Phase I human clinical trials, a small few in Phase II, and none passing Phase III (Hans, D et al., *Medicinal Chemistry* 2006, 2:627-46).

The candidate viral subtypes for annual flu vaccine update do not include the mainly avian infective H5N1, which have historically infected poultry. However, investigators at Scripps Research Institute and others have identified the Egret/Egypt/1162/NAMRU-3/06 as a variant having likely human infective potential (Stevens, 2008, above). In fact, reports of the H5N1 viruses infecting humans are increasing. Because of the lack of exposure to related sub-strains, an H5N1 infection in a human often has severe effects. The recently emerging ability of the virus to infect humans is thought to be attributable to the conversion from a SAα2-3Gal to SAα2-6Gal receptor recognition by the virus. Investigators have found that H5N1 virus that infected humans is capable of recognizing both types of receptors (Yamada, S et al., *Nature* 2006, 444:378-82).

Although helpful to an extent in preventing the disease, the success of the WHO's Influenza Program is limited for several reasons. One such reason is the limited number of surveillance locations and a small sampling size compared to the occurrence of influenza infection (in 2004-2005, about 6000 samples, or 1 sample per 100,000 cases). Another drawback is the time it takes to prepare vaccines once such candidate antigenic subtypes have been selected (Layne, *Emerging Infectious Disease* 2004, 12(4): 562-568). Added to the difficulties is the above-mentioned antigenic drift and shift. New strains may appear at any time.

Another complicating phenomenon is broadening of the immune response via the process of epitope spreading, where a host's immune system over time changes target of the immune attack to nearby epitopes (N. Suciu-Foca et al., *Immunol. Rev.* 1998, 164:241). Thus, the inability to modulate the relevant antigenic determinants over time renders simple vaccines ineffective in a short time.

Therefore, a new method for developing and preparing vaccines that are effective under these circumstances are needed.

Strategy for Creating Active Peptides

In recent years, vaccines based on synthetic peptide epitopes rather than whole antigenic molecules have been explored and developed, in the hope of more refined targeting and ease of achieving consistent quality, as well as the safety of being non-infectious. The results are mixed. As a practical matter, it is time- and resource-intensive to identify one peptide or a set of a limited number of peptides that would be effective as a vaccine. In addition, because of the infectious agents' immune evasion strategies briefly described above, peptide epitope-based vaccines have not overcome the shortcomings of traditional vaccines. Investigators have attempted to make use of conserved epitopes within the virus. These regions do not mutate, and thus represent an approach for the generation of broad-spectrum, peptide-based vaccines (Ben-Yedidia, 2007, above). These approaches using short peptides; however, the invoked immunity is T cell-based, requires adjuvant or carrier proteins (flagella) and lacks the proven pathogen fighting ability of preexisting antibodies (Zinkernagel, R M, Nobel Lecture Dec. 8, 1996).

The development and exploitation of combinatorial chemistry (CC) has propelled drug discovery. Drug discovery can be generalized into two major steps, lead generation and lead optimization. Oftentimes, a lead compound is identified that has some of the desired characteristics of a commercially viable therapeutic, but has shortcomings such as a low specific activity, toxicity, instability, etc. Thus, once a lead is identified, practitioners attempt to optimize the lead compound by testing other related compounds with similar structures. CC allows practitioners to create and quickly screen a library made of a vast number of candidates, to identify those with a specific activity against a target of interest.

For peptide based drugs, the goal is to define a single, or a limited set of peptides which demonstrate a particular activity. The art of CC as applied to the synthesis of peptide libraries, too, has advanced, producing highly reliable and pure mixtures of peptides of great diversity. The process of identifying the single or limited set of peptides that were responsible for the observed activity from such diverse libraries, called deconvolution, is schematically represented in FIG. 1A.

Drug discovery based on CC are powerful, but deconvolution can be difficult and time- and cost-intensive. Thus, to simplify deconvolution and make the process more efficient, practitioners have spent great efforts to create suitable synthesis methods. Examples of the resulting evolution of subtypes of combinatorial methods include: multiple synthesis, iterative synthesis, positional scanning, and one-compound-one-bead post assay identification design. They are briefly described below to show the state of the art and how peptide epitopes were successfully identified.

"Multiple synthesis" provides for any method whereby distinct compounds are synthesized simultaneously to create a library of isolated compounds. The identity of these compounds would be known from the rules of the synthesis. An example is found in H. M. Greysen et al., *Proc. Nat. Acad. Sci. USA,* 1984, 81:3998, where the investigators identified GDLQVL (SEQ ID NO: 20), out of 108 overlapping peptides, as the epitope recognized by an antibody raised against VPI protein of foot-and-mouth disease virus.

"Iterative synthesis/screening" involves methods of peptide synthesis which facilitates the determination of the peptide sequences as deconvolution is performed. This is done by synthesizing pools of peptides, each pool consisting of peptides with the two amino terminal residues defined and known to the investigators. These peptides can be shown as $O_1O_2XXXX$, wherein O1 and O2 are the defined residues and X is randomly selected. When a pool that contains a peptide that binds to a target is identified, the two amino terminal residues are known. The next step was to do the same for position three, by synthesizing peptides that can be shown as F $F_2O_3XXX$, wherein 03 is a fixed residue. Subsequent residues are determined in a similar manner. An example of iterative synthesis can be seen in R. A. Houghten et al., *Nature* 1991, 354:84-86, wherein the investigators honed in on the sequence DVPDYA (SEQ ID NO: 21) as the core epitope after identifying YPYDVPDYASLRS (SEQ ID NO: 22) using an ELISA type assay format.

"Positional scanning" is a synthesis method producing complex mixtures of peptides that allows for the determination of the activity of each individual peptide. Based on the screening results, the derived peptide can then be separately synthesized for optimization. As seen in C. Pinilla et al., *Biochem J.* 1994, 301:847-853, positional scanning libraries were used to identify decapeptides which bound the same YPYDVPDYASLRS-binding antibody (SEQ ID NO: 22). In this case ten different libraries each containing 20 pools with a defined amino acid at each of the ten positions in the peptide. Fifteen peptides were identified.

Each of the above methods were also employed to identify enzyme substrates (J. H. Till et al., *J. Biol. Chem.* 1994, 269:7423-7428, J. Wu et al, *Biochemistry* 1994, 33:14825-14833, W. Tegge et al., *Biochemistry* 1995, 34:10569-10577) or enzyme inhibitors (M. Bastos et al., *Proc. Nat. Acad. Sci. USA* 1995, 92:6738-6742, Meldal et al., *Proc. Nat. Acad. Sci. USA* 1994, 91:3314-3318, R. A. Owens et al., *Biomed Biophys. Res. Commun.* 1994, 181:402-408, J. Eichler et al., *Pept. Res.* 1994, 7:300-7).

As powerful and clear-cut the identification of a specific peptide may be, as a therapeutic, such identified peptide may only be a lead peptide that is not itself useful. The identified peptide epitope may be ignored by the immune system if it resembles a self protein or possibly exacerbate the very condition that the therapy aims to relieve. However, by designing peptides of similar sequence, one may create, based on such peptide, epitope reactive analogs that would act as modifiers of the immune responses and/or as excitors of an immunogenicity response.

One such approach is creation of altered peptide ligands (APL). This approach is schematically represented in FIG. 1B. An APL is defined as an analog peptide which contains a small, number of amino acid changes from a starting sequence such as that of a native immunogenic peptide ligand. While recognition of the native response may induce an antagonist-like reaction, an APL might also induce a partial agonist response, or induce a state of anergy in the reactive T cell population. In discussing APL in the context of allograft rejection therapy, Fairchild et al., *Curr. Topics Peptide Protein Res.* 2004, 6:237-44, note that an APL acting as an antagonist for one TCR, may become an agonist for another, complicating the rational design of an APL. Compounding the obstacle of the development of APL is the difficulty in translating a response developed in an animal system into human.

An illustrative example is an APL based on an epitope of myelin basic protein, MBP83-99 (ENPVVHEF KNIVTPRTP (SEQ ID NO: 23)), which is reported to be a target of autoimmune response causing multiple sclerosis. APLs were made by replacing the bold and underlined amino acid residues "E", "N", "E" and "K," resulting in identification of a single peptide having the amino acid residue sequence AKPVVHLFANIVTPRTP (SEQ ID NO: 24) that appeared to have the desired activity of neutralizing antibodies against MBP83-99, Kim et al. *Clinical Immunology,* 2002, 104:105-114. The peptide was placed into limited human trials, which reportedly resulted in the long term immune reactivity against the peptide, but the treatment has been deemed clinically ineffective by evaluation using MRI. Thus an APL, once identified, can be used as a therapeutic agent; however, its effectiveness may be limited in terms of clinical efficacy.

Evasive Targets

In the context of developing vaccines in the prevention of infectious disease, the invading pathogens have acquired by natural selection the ability to quickly create variability in the relevant immunogenic epitope. Examples of viral mutants generating escape variants that avoid immune detection have been reported for Hepatitis B, influenza, and HIV (Tabor, E, *Journal of Med. Virol.,* 2006, 78:S43-S47; Daniels, R S et al., *EMBO Journal* 1987, 6:1459-65; D'Costa, S et al., *AIDS Res Hum Retroviruses* 2001, 17:1205-9). This variation progressively dampens the utility of single-epitope vaccines.

Thus, investigators have attempted to overcome this limitation by introducing variance by creating a mixture of immunity-inducing epitopes to be used as vaccines. Furthermore, it has previously been shown that mixtures of related peptides may be therapeutically more effective than a single peptide. Lustgarten et al., *J. Immunol.* 2006, 176: 1796-1805; Quandt et al., *Molec. Immunol.* 2003, 40: 1075-1087. The effectiveness of a peptide mixture as opposed to a single peptide is the likelihood of interaction with the broadening of the relevant epitopes via evolution-induced variation. Therefore, to increase and maintain the longer-term effectiveness, these previous treatment modalities have been modified. For example, a therapeutic composition based on an APL may include multiple peptides created by the APL method in combination with the original peptide, or other APLs. Fairchild et al., *Curr. Topics Peptide & Protein Res.* 2004, 6:237-44. Each APL would have a defined sequence, but the composition may be a mixture of APLs with more than one sequence. A reverse example involving conceptually similar altered peptide ligands involves an inventor's attempt to reduce the amount of variation created by pathogens to avoid immune recognition (viral alteration of immunogenic epitopes over time, e.g., the creation of altered peptide ligands), by using the very changes created by the pathogen in an epitope sequence to create a limited diversity pool of peptides potentially useful in vaccinations (U.S. Pat. No. 7,118,874). In this invention, distinct hyper-Variable region sequences from HCV or influenza virus were compared. The amino acid changes having a frequency greater than 12% were incorporated into a mixture of between 2 and 64 different peptides.

However, a simple mixture of several soluble peptide epitopes faced certain manufacturing issue of soluble peptide mixtures, such as difficulties in delivering a consistent ratio and quantity of each of the peptides in the mixture.

Peptide dendrimers were conceived to overcome some of these shortcomings of soluble peptide mixtures, and also by providing other perceived advantages. This approach is schematically represented in FIG. 1C. The design of dendrimers intends to mimic two traits of naturally occurring biological structures: a globular structure and polyvalency to amplify the ligand:substrate interaction. Beyond these commonalities, dendrimers are chemically and structurally diverse, with reports of a wide range of sizes, from 2 kDa to greater than 100 kDa. Dendrimers are described in two comprehensive reviews (P. Niederhafner et al., *J. Peptide Sci.* 2005 December; 11(12):757-788; K. Sadler and J. P. Tam, *Rev. Mol. Biotechnol.* 2002, 90:195-229), and their applications in additional literature (D. Zanini and R. Roy, *J. Org. Chem.* 1998, 63:3468-3491; J. Haensler and F. C. Szoka, *Bioconjug Chem.* 1993, 4:372-379; Tam, James P et al., *J. Exp. Med.* 1990, 171:299-306).

Despite attempts and a certain amount of success in utilizing dendrimers and some improvements in synthesis and purification strategies, a high cost of manufacturing and the subsequent analytical development precludes this technology from being further currently developed commercially.

All of the above strategies, while recognizing the advantage of variations in the therapeutic peptide compositions, derive from the concept that there is one or more defined peptide sequences evoking a defined immunological response. These strategies have attempted to multiply and diversify modulatory peptides via the introduction of defined, single changes performed one at a time.

An entirely different approach which has evolved alongside the defined sequence peptide immunotherapy approach is the use of random epitope polymers. Random sequence polymers (RSP) can be described as a random order mixture of amino acid copolymers comprising two or more amino acid residues in various ratios, forming copolymers by random sequence bonding, preferably through peptide bonds, of these amino acid residues, which mixture is useful for invoking or attenuating certain immunological reactions when administered to a mammal. Because of the extensive diversity of the sequence mixture, a large number of therapeutically effective peptide sequences are likely included in the mixture. In addition, because of the additional peptides which may at any given time not be therapeutically effective, but may emerge as effective as the epitope shifting and spreading occurs, the therapeutic composition may remain effective over a time of dosing regimen. This approach is schematically represented in FIG. 1D.

Copolymer-1 (also known as Copaxone®, glatiramer acetate, COP-1, or YEAK random copolymer) is an FDA approved, commercially available therapeutic used for the treatment of multiple sclerosis comprising random copolymers of Y, E, A, and K. Random copolymers are described in International PCT Publication Nos. WO 00/05250, WO 00/05249; WO 02/59143, WO 0027417, WO 96/32119, WO/2005/085323, in U.S. Patent Publication Nos. 2004/003888, 2002/005546, 2003/0004099, 2003/0064915 and 2002/0037848, in U.S. Pat. Nos. 6,514,938, 5,800,808 and 5,858,964. It is one of the few therapeutics for multiple sclerosis that continues to be effective over time.

Attempts continue to build on the success of COP-1 by creating other RSPs and related peptide compositions. WO/2005/074579 (the '579 publication) describes complex peptide mixtures of various amino acid composition. The disclosure also contains diversity-constraining mechanisms of defining amino acids at certain positions rather than being chosen by the random nature of the synthesis rules. Another such attempt is the work originated by Strominger et al. (WO/2003/029276) and developed further by Rasmussen et al. (US 2006/0194725) wherein they created RSP consisting of the amino acids Y, F, A, and K with different amino acid ratios and a shorter average length than COP-1 Alanine content was increased based on Maurer (Pinchuck and Maurer, *J. Exp Med* 122(4), 673-9, 1965), which described how an EAK polymer with higher alanine content (10-60 mole percent) produced "better antigens"; Rasmussen et al. in fact demonstrated that a YFAK input ratio of 1:1:1:1 was not effective in eliciting a recall response as compared to a YFAK preparation with an input ratio of 1:1:10:6.

WO/2005/032482 (the '482 publication) describes another approach, which is to build degenerate peptide sequences based on motifs, exemplified by [EYYK]. The motifs are used as is, or can be altered by amino acid substitutions (defined on page 10-11 of the '482 publication). A significant difference from COP-1 is that it lacks alanine. Much of the invention hinges on the presence of a D-amino acid at the amino terminal of the motif.

Tracing back steps to the defined peptide search, there have also been attempts to identify the active peptide(s) within the RSP mixture. The drawback of this technology lies in the very nature of the attempt to determine discrete substitutes for the randomness that COP-1 encompasses.

Effective as the random sequence polymer approach may be, even the improvements have not resolved the drawback and limitation of COP-1, which is, for example, the undefined nature of what is effective in each motif and the possibility of containing a large proportion of truly inactive peptides, lowering the concentration of the active components, or worse, adversely stimulating the immune system. Additionally, these compounds are difficult to manufacture and to obtain consistency from lot-to-lot.

All these approaches have not overcome the shortcomings of previously existing systems, and need remains for a composition and a method to create such composition that would serve effectively as a vaccine by eliciting beneficial immune responses consistently and over time toward pathogens, for which existing vaccine compositions have failed to be effective.

SUMMARY OF THE INVENTION

The instant invention comprises a process for designing, manufacturing, and administering a composition comprising directed epitope peptide mixtures useful for eliciting immune responses in the up-regulation of immune function in the treatment of infectious disease, such process defined by a set of rules regarding the identity and the frequency of occurrence of amino acids that substitute a base or native amino acid of a known sequence, or epitope. A method of the instant invention uses a sequence of a known sequence, or epitope as a starting point. The amino acids that make up the epitope are modified via the introduction of different, related amino acids defined by a set of rules. The result is a mixture of related peptides useful in and of itself as a therapeutic, which is described herein as a composition comprising "directed-sequence polymers" or "DSP". Such composition is referred to as a "DSP composition." The method of synthesizing a DSP composition utilizes and maintains the natural order of amino acid residues of a defined peptide sequence of a specified length. Each amino acid position is subjected to change based on a defined set of rules. In a preferred embodiment the amino acid is substituted according to the methods described in Kosiol et al., *J. Theoretical Biol.*, 2004, 228:97-106. Alternatively, amino acids can be changed in accordance with the exemplary substitutions described in PCT/US2004/032598, page 10-11. Alternatively, amino acids can be changed in accordance with the differences at a given position between variants within a given pathogen. Alternatively, amino acids can be changed in accordance with the differences at a given position between variants of sub-species of a given pathogen.

For the solid phase synthesis procedure of the instant invention, the mixture of amino acids for a given position in the peptide is defined by a ratio of one to another. Prior to starting the synthesis, such ratio is determined for each position along the peptide. The resulting directed order peptide mixture comprises a multiplicity of related peptide sequences.

The length of a DSP can be one of the original defined sequence peptide or, generally any length up to up about 30 repeated lengths of the original defined sequence peptide, but is dictated by the total length of the desired end product. The length of the full length of a DSP sequence can be between about 25 and about 300 amino acids, and preferably between about 45 and 70 amino acids.

When considering the entire length of a DSP, the percentage of alanine as compared to all of the other amino acids in the DSP combined is greater than 5% on average, and will not exceed 90% on average. Preferably, the alanine percentage is between 10% and 70% on average. More preferably the percentage of alanine is between 15% and 35% on average.

When considering a "cassette" comprising the DSP that is less than the entire length of the DSP, the percentage of alanine as compared to all of the other amino acids in the section of the DSP will always be greater than 1% on average, and will not exceed 99% on average. Preferably, the alanine percentage is between 5% and 95% on average. A cassette is a synthesis unit of DSPs with a defined relative amino acid ratio, and comprises a sequence of an identified epitope.

The complexity of the mixture is greater than $5\times10^2$ different peptides. In a further embodiment, the complexity of the mixture is greater than $1\times10^4$ different peptides. In a further embodiment, the complexity of the mixture is greater than $1\times10^6$ different peptides. In a further embodiment, the complexity of the mixture is greater than $1\times10^8$ different peptides. In a further embodiment, the complexity of the mixture is greater than $1\times10^{10}$ different peptides. In a further embodiment, the complexity of the mixture is greater than 1×10$^{12}$ different peptides. In a further embodiment, the complexity of the mixture is greater than 1×10$^{14}$ different peptides.

In some embodiments, the base peptide sequence from which the DSP sequences are derived is selected from a group consisting of SEQ ID NO: 1-7 depicted in Table I.

In other embodiments, such base peptide sequence is an epitope relevant to the pathology of a viral infectious disease selected from the group consisting of AIDS, AIDS Related Complex, Chickenpox (Varicella), Common cold, Cytomegalovirus Infection, Colorado tick fever, Dengue fever, Ebola haemorrhagic fever, Hand, foot and mouth disease, Hepatitis, Herpes simplex, Herpes zoster, HPV, Influenza (Flu), Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever.

In particular, the present invention is well suited for developing and preparing influenza vaccines. Exemplary sequences of influenza HA protein are SEQ ID NO: 8-16, from which partial sequences can be selected based on further examples described herein as epitopes and thus as the base sequences for the present invention.

In other embodiments, such base peptide sequence is an epitope relevant to the pathology of a bacterial infectious disease selected from the group consisting of Anthrax, Bacterial Meningitis, Botulism, Brucellosis, Campylobacteriosis, Cat Scratch Disease, Cholera, Diphtheria, Gonorrhea, Impetigo, Legionellosis, Leprosy (Hansen's Disease), Leptospirosis, Listeriosis, Lyme disease, Melioidosis, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus (including epidemic typhus), and Urinary Tract Infections.

In other embodiments, such base peptide sequence is an epitope relevant to the pathology of a parasitic infectious disease selected from the group consisting of Amoebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amoebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Plasmodium, Scabies, Schistosomiasis, Taeniasis, Toxocariasis, Toxoplasmosis, Trichinellosis, Trichinosis, Trichuriasis, Trichomoniasis, and Trypanosomiasis (including African trypanosomiasis).

Another embodiment of the invention is based on the base peptide sequence relevant to prion-diseases. SEQ ID NO: 17 is human prion protein sequence. A relevant peptide is selected from partial sequences of SEQ ID NO: 17.

Another aspect of the invention is a process for preparing a composition comprising DSPs described above, wherein the naturally occurring immune response is inadequate for preventing or overcoming the pathology associated with the epitope for which the immune response is elicited.

One aspect of the present invention is a pharmaceutical composition comprising a DSP composition, optionally as a pharmaceutically acceptable salt. In a preferred embodiment, such pharmaceutical composition comprising a DSP composition, when administered to a subject, causes a favorable modification of otherwise limited and inadequate immune response in the subject desirous of such a modification, such as an increase in appropriate immune responses.

Another aspect of the present invention is a method of enhancing immune responses by administering a DSP composition to a subject in need thereof. In a particular embodiment, the subject exhibits only a limited and inadequate immune response to undesirable pathogens. In certain embodiments, the subject is in need of such administration because of an infectious disease or similar disorder that can be recognized by one of ordinary skill in the art. Another aspect of the present invention is a method of treating a diminutive immune response by administering a DSP composition comprising base peptide sequences that are unrelated to the pathogen of interest and that are useful in boosting generalized immune function.

Yet another aspect of the invention is a method of protecting a subject from an influenza infection wherein the influenza virus is a new immunologic subtype comprising the step of administering a pharmaceutical composition comprising a DSP composition the base sequence of which comprises an epitope from hemagglutinin of an influenza virus subtype that caused the most immediate past epidemic at any given time when such protection is desired. The new immunologic subtype may be an antigen drift or antigen shift.

A still further embodiment of the instant invention is a method of designing, manufacturing, and administering a vaccine directed against all the variants of the most recently dominant cluster of related influenza virus. Said virus may derive from influenza A, B, or C, and may be influenza A subtype H3N2, H1N1, or H5N1 or a future shifted variant thereof.

BRIEF DESCRIPTION OF THE DRAWINGS

FIG. 4 shows the preferred defined substitutive rules for directed expansion of epitope permeability.

FIG. 5 shows a generic rule structure and ranges of substitutions of DSP synthesis.

FIG. 6 shows an example of the application of the DSP Synthesis Rules using a mock-source peptide.

FIG. 7A-E shows examples of the application of the DSP Synthesis Rules using influenza epitopes as source peptides. FIG. 7D discloses SEQ ID NO: 26.

DETAILED DESCRIPTION OF THE INVENTION

Figure 1:
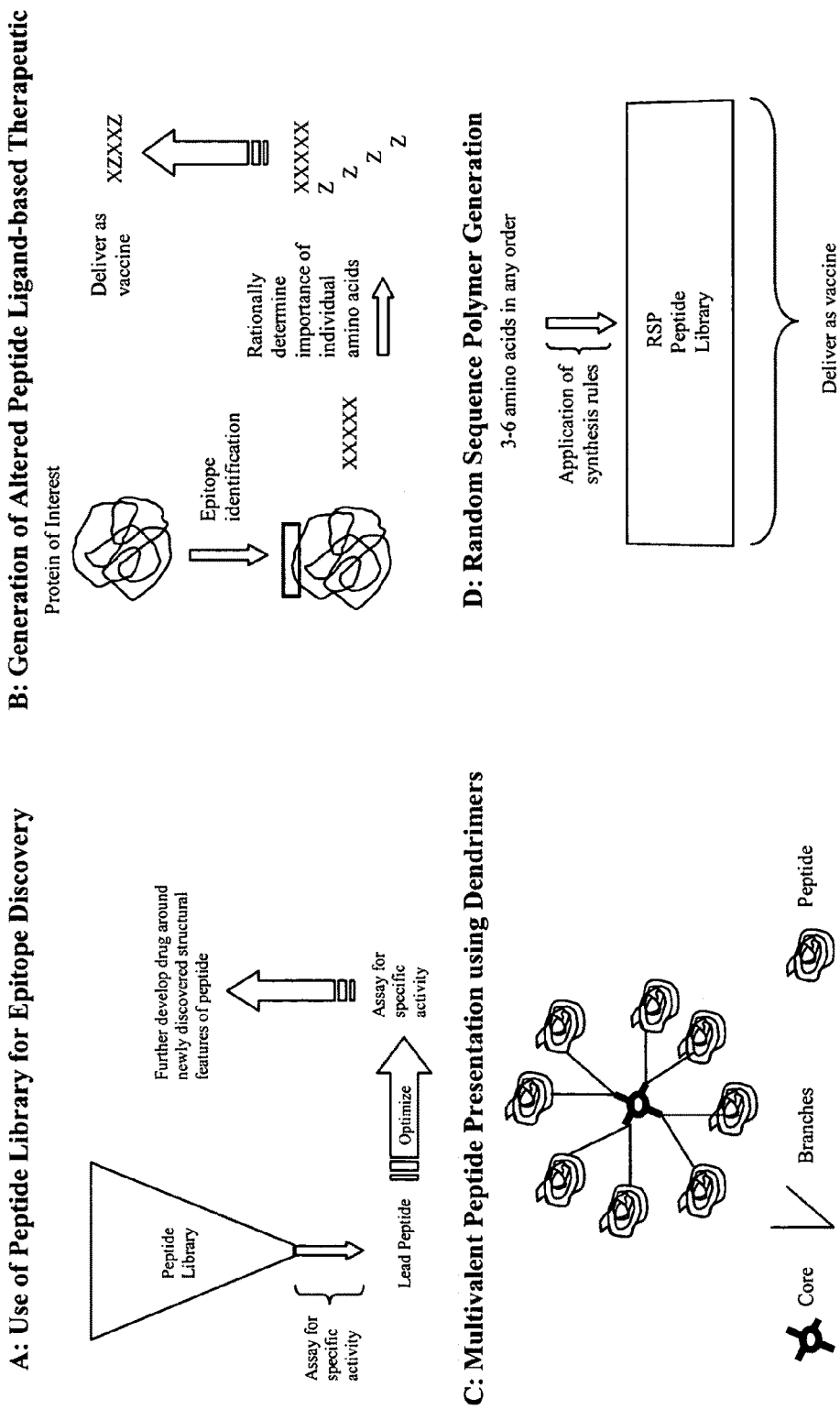
FIG. 1A-D is a schematic depicting methodologies for designing synthetic peptide-based therapeutics. Panel A: how a peptide library is used for epitope discovery; Panel B: conceptual steps for generating Altered Peptide Ligand-based therapeutic; Panel C: a schematic of a dendrimer for multi-valent peptide presentation; Panel D: random sequence polymer generation.
Figure 2:
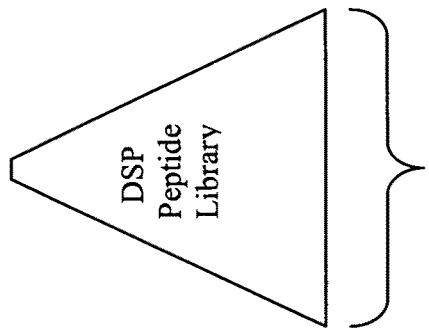
FIG. 2 is a schematic for conceptual steps for generating Directed-Sequence Polymers.
Figure 3:
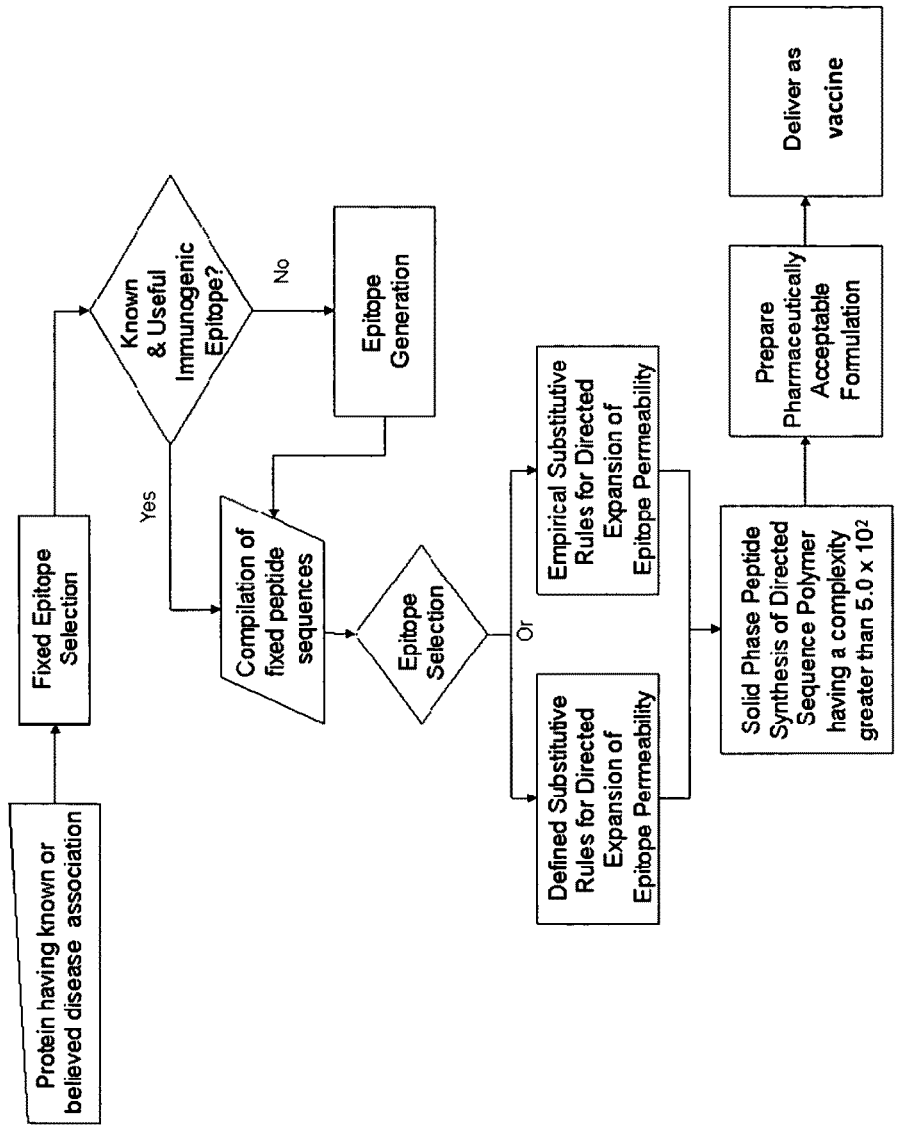
FIG. 3 shows the steps for preparing Directed-Sequence Polymers.

The instant invention draws out the most useful properties of the previous treatment modalities yet removes the limitations of each. The instant invention utilizes: (1) the specific immunologic relevance of a defined epitope peptide, (2) the modulatory properties of an APL, (3) the desirable multi-valency, (4) and the alanine content from RSP to generate a directed expansion via alteration and degeneration of epitope variability that forms a complex yet directed peptide library useful for delivery as a vaccine. The approach is schematically represented in FIG. 2.

The instant invention relates to a "Directed-Sequence Polymer" (DSP). A DSP is a peptide within a library of related peptides having a sequence derived from a base peptide sequence, which may be but not limited to a native epitope associated with a desired immune response. A DSP has one or more amino acid residue that differs from that of the base peptide sequence, the substitution of which is determined by a defined rule. A DSP composition comprising multiple DSPs is synthesized by applying a set of synthesis rules that define the amino acid variations and the ratio of occurrence of introduction of such amino acid residues at any given position of the sequence to the base peptide sequence. Thus, a DSP is not synthesized as a single peptide, but is always synthesized as part of a composition comprising multiple related DSPs, the overall mixture of which is reproducible and consistent with the rules of synthesis that were applied. The schematic for the steps for creating a DSP composition, starting from the choice of a base peptide, is shown in FIG. 3.

I. Base Peptide Sequences

To create a meaningful DSP composition, one first needs to define the base peptide sequence to derive the DSPs from. The base peptide sequences can be derived in many ways. A peptide sequence useful for this purpose is a peptide sequence related to immune response in a mammal. Alternatively, the base peptide sequence can be derived from the group consisting of a virus, bacteria or parasite. Further examples of peptide sequences are, for example, empirically derived peptide sequences, such as through screening of library created by combinatory chemistry.

Infectious Disease-Derived Base Peptide Sequences

As briefly touched in the Background section, the use of vaccines to combat infectious diseases has been the classic paradigm of immunotherapy. However, not all known and significant infectious agents are readily treated with vaccines created by conventional methods. Epitopes that are therapeutically and prophylactically effective may be cryptic, or they may change so frequently as to render a developed vaccine ineffective and irrelevant. Rapidly evolving viruses would mean the number of people carrying the virus with same immunological profile becomes small, fragmenting the patient population against which a vaccine may be effective. Moreover, chronic infections caused by agents such as HIV, hepatitis C virus (HCV), and human papillomavirus (HPV) may require a different approach to immune elicitation due to the fact that they evolved to evade immune systems and are poor antigens.

As described in the Background section, one of the most evasive infectious agents is the influenza virus. The humoral human immune system recognizes two major immunogenic proteins from the virus, hemagglutinin (HA) and neuraminidase (NA). The known epitope regions of the head or top of the HA molecule correspond to the hypervariable regions These sequences are highly mutable and in fact isolated sequences have variations within this region.

Another epitope thought to be potentially useful as a target for flu vaccine is the extracellular peptide M2e of the integral M2 protein, conserved in all influenza A strain. Ben-Yadidia, T. and Amon, R., 2007*, Expert Rev. Vaccines* 6(6):939-948.

Current therapeutic regimens for HIV treatment comprise immunization using clade B gag, protease, reverse transcriptase, gp120 and nef peptides and lipopeptides, both by expression of these proteins using expression vectors and by direct immunization. Other immunogenic and therapeutically promising HIV proteins are gp41 and env proteins.

Unlike Hepatitis A and Hepatitis B, for which there are effective vaccines and antibody treatments available, Hepatitis C has evaded immune responses. Vaccines based on envelope glycoprotein (E1/E2) and virus-like particles have met limited success.

The peptide sequences of these proteins and epitopes have been extensively investigated and are readily available to one skilled in the art. See, for example, Berzofsky et al., *J. Clin. Invest.* 114:450-462 (2004) for a review with citation of these proteins. Further, Immune Epitope Database and Analysis Resources (http://www.immuneepitope.org), particularly useful for obtaining data and analysis of influenza HA and NA proteins.

Examples of epitopes identified as part of a naturally occurring, full length protein or synthetic peptides that were identified to have similar activities as such epitopes are shown in the table below.

TABLE I

Examples of epitopes

| Peptide Sequence | Source/Original Protein | Residue Number | Ref | SEQ ID NO: |
|---|---|---|---|---|
| ILARNLVPMV | human cytomegalovirus HCMVpp65 | 491-500 | 1 | 1 |
| ELEGVWQPA | HCMVpp65 | 526-534 | | 2 |
| RIFAELEGV | HCMVpp65 | 522-530 | | 3 |
| NLVPMVATV | HCMVpp65 | 495-503 | | 4 |
| RIQRGPGRAFVTIGK | HIV-gp120 | V3 loop | 2 | 5 |
| IIPKSSWSDHEASSGVSSACPYQ GRSSFFRNVVWLIKKDNAYPTIK RSYNNTNQEDLLVLWGIHHPNDA AEQTRLYQNPTTYISVGTSTLNQ RLVPKIATRSKVNGQSGRMEFF WTILKSNDAINF | Influenza virus HA protein H5 Accession Number ACD62257 | 115-240 | 3 | 6 |

TABLE I-continued

Examples of epitopes

| Peptide Sequence | Source/Original Protein | Residue Number | Ref | SEQ ID NO: |
|---|---|---|---|---|
| CIIPKSSWSDHEASSGVSSACPY QGRSSFFRNVVWLIKKDNAYPTI KRSYC | Influenza virus HA protein H5 Accession Number ACD62257 | 115-163 flanked by cysteines | | 7 |

Empirically Derived Base Peptide Sequences

As described in the above sections, peptide sequences with some significance to a disease state or an adverse reaction may be identified through experimental investigation of a relevant epitope. These sequences may include non-naturally occurring peptide sequences that proved to be useful in treating a disease or a condition, an example found in the international patent application publication WO 2006/031727, U.S. Pat. No. 6,930,168 and the related scientific publication by Stern et al., *Proc. Nat. Acad. Sci. USA,* 2005, 102:1620-25.

Further, epitopes are empirically determined by identifying candidate sequences by positional scanning of synthetic combinatorial peptide libraries (see, for example, D. Wilson et al., above; R. Houghten et al., above; Hernandez et al., *Eur. J. Immunol.,* 2004, 34:2331-41), or by making overlapping peptide sequences of the entire protein of interest, and testing those peptides for immune reactivity using, for example, any readout assay useful for such purposes, such as the HI assay, a viral challenge model, or one described in Current Protocols in Immunology Edited by John E Coligan, Ada M Kruisbeek, David H Margulies, Ethan M Shevach, Warren Strober N I H, John Wiley & Sons, in an in vitro or in vivo assay system appropriate for the disease and species the epitope is sought for. Candidate molecules may include peptides that are modified during or post-synthesis by, for example, sugar- and modified sugar addition such as glycosylation and glycogenation either N or S-linked, fatty acid modification such as myristoylation, or containing disulfide bonds.

After identifying a candidate epitope, a probable set of additional related epitopes are generated using sub-strain variants, cluster variants, drift variants, shift variants of a pathogen, or via modeling and prediction algorithms described in readily available references, for example WO 2000/042559, align and analyze the mutations, probable anti-body accessible epitopes, or predicted binding of these probable epitopes using available prediction methods described in, for example, WO 2005/103679, WO 2002/073193 and WO 99/45954. Selecting from the peptides having the highest predicted activity/binding, take 40% of the predicted sequences and acquire the percentage of any given amino acid at each position. Use those percentages to create the rules for amino acid incorporation into a DSP synthesis.

II. Rules of Synthesis for Directed-Sequence Polymers

Steps in the creation of a DSP sequentially encompass the following:

(a) Identify a protein having known or believed association with a pathology.

(b) Select from within the protein a peptide or peptides, each having a fixed sequence, that are associated with the pathology and immunologically relevant. If no peptides have been described, then peptides useful in the treatment of the pathology of interest are created. One exemplary method is to create a library of peptides that collectively span the entire length of the protein of interest. This may be done by, for example, partial endopeptidase digestion or by peptide synthesis. The peptides may be further chemically modified by, for example, sugar- and modified sugar addition such as glycosylation and glycogenation, fatty acid modification such as myristoylation, or introducing disulfide bonds. The library is screened for immunologically relevant peptides using appropriate detection methods such as the functional assays HI, or viral challenge, or via binding affinity determination using antibodies detected in the sera of patients with the target pathology. The peptides may be further examined for immunogenicity useful for the treatment of the pathology in an in vitro or in vivo experimental system.

(c) the amino acid substitutions are decided based on either of two sets of rules, defined or empirical, and are set forth below;

(d) Solid phase synthesis of DSP according to the rules is performed, and pharmaceutically acceptable formulation the DSP is delivered as a vaccine.

The rules of synthesis for a composition comprising DSPs are outlined below. Briefly, a DSP may be envisioned as a polypeptide having a defined length that is either the same length as or multiples of the length of the base peptide sequence. For selected residue positions of the base peptide sequence, one or more substitute residue is defined. The rule of synthesis defines the ratio among the original base peptide residue for that position, the first substitute residue, the second substitute residue, the third substitute residue, the fourth substitute residue, the fifth substitute residue, the sixth substitute reside, and an alanine, to occupy any given residue position.

The substitute residues are defined: (1) according to a rational comparison and finding of similarities of relevant characteristics of the original residue with those of the substitute residue, (2) in accordance with the differences at a given position between species (including, in case of microbes, "serotypes" and "immunological subtypes", (3) in accordance with the differences at a given position within variants of the same species, or (4) to a comparison of reported experimental results on the relative activities of actual peptides having slight variations from the base sequence. The substitute residues defined in any of these approaches are termed "conserved substitution" herein.

An example of a rational comparison and findings of similarity is the methods described by Kosiol et al., *J. Theoretical Biol.,* 2004, 228:97-106. Amino acids are grouped together in a matrix, referred therein as PAM replacement matrix. FIG. 4 is a table showing the amino acid similarity and grouping, according to Kosiol, based on the characteristics of the residues such as size, charge, hydrophobicity, etc. In FIG. 4, amino acids grouped together are considered interchangeable, with high likelihood of retaining characteristics common among the group, A comparison of experimental results showing the relative activities of peptides having slight variations from the base sequence can also be used as a basis for the rule for substitution. The sequences of the peptides responsible for observed changes are aligned and the type and percent presence of the new amino acid are noted. If there is more than one amino acid substitution at any given position of the peptide, the frequency of occurrence of an amino acid and the magnitude of activity change compared to the original sequence are taken into account to determine the order of prevalent substitution. Examples of the overall process leading up to the rule generation for DSP synthesis can be found using libraries (*Molec. Immunol.* 40:1047-1055; *Molec. Immunol.* 40:1063-74; *J Autoimmunity* 20:199-201; and *J. Immunol.* 163:6424-34), by making altered peptide ligands of overlapping peptides representing the entire protein of interest (Atkinson et al., *J. Clin. Invest.* 94:2125-29; Meini et al., *J. Clin. Invest.* 92:2633-43) or de novo (U.S. Pat. Nos. 7,058,515; 6,376,246; 6,368,861; 7,024,312; 6,376,246; 7,024,312; 6,961,664; 6,917,882). Briefly, a cellular material of interest is chosen as the assay system to rank the immunoreactivity of the peptides to be interrogated. Such an assay system can be either an in vitro or in vivo system, and can comprise adaptive or innate immune reactivity. Readouts for the assay system can be the up- or down-regulation of the status of the activation state of a protein, a change in the localization of a protein, the expression of the mRNA encoding for the protein, the relative concentration of a protein, changes in the generation of specific cell types, changes in cellular phenotype, changes in cellular activation, changes in cell number, changes in organ size or function, changes in animal behavior or phenotype, hemagglutination of red blood cells, or survival. Once the assay or assays are performed the results are analyzed to determine the prevalence of any particular amino acid as a conserved substitution. If more than six residues in a given position within the peptide sequence are identified as generating a change in immunologic function, the top six residues first by frequency of representation in the interrogated peptides, and second by the magnitude of changes elicited. Once chosen, the relative amounts of the residues are defined. As depicted in FIG. 5, each cassette, "y", has a set of amino acid ratios one to another that have a range of about 0-100 for the base (a), the primary change (b), the secondary change (c), and the tertiary change (d), whereas alanine (e) has a ratio of about 0.5-100.0. If existing or desirable number of changes are larger, quaternary and further advanced changes up to 10 amino acids may be incorporated. The rules for the DSP synthesis continue with the combination of the cassettes in the order prescribed. The same block can be repeated either sequentially or separated by another block. On either side of the cassette sequence are N- and C-terminal modifiers. The number of cassettes is dictated by the requirements of the end length of the DSP which is required to be longer than 25 amino acids and shorter than 300 amino acids. Preferably, the full length of the DSP is between about 30 amino acids to 150 amino acids. More preferably, the full length of the DSP is between about 45 amino acids to about 70 amino acids.

As described in FIG. 6, the instant invention envisions multiple epitopes to be defined as separate cassettes and synthesized sequentially. Cassette ratios within the same DSP may have different ratios of amino acids. Further, if there are less than three non-alanine amino acid substitutions, the percentage of the 'missing' substitution is added to the base sequence. Further, a cassette may be placed in any order with multiple appearances in the overall DSP synthesis. The N- and C-terminal modifications reside prior to and after the entirety of the DSP cassettes respectively. As seen in FIG. 7A, a single base peptide sequence may have more than one ratio defined as a separate cassette in this example y1, y2, and y3. The individual cassettes can be placed in any order with multiple appearances in the overall DSP synthesis as seen in FIG. 7B.

A cassette may be repeated more than once. After a desired number of multiples of the cassette, if the desired length of the DSP is not yet reached, the DSP sequence is further defined by applying the same process, possibly using different ratio among the original, substitute, second substitute, and alanine residues.

N or C-terminal DSP modifiers may be added to the synthesis rules. The purpose of such modifiers include but are not limited to enhancing immunogenicity such as KLH, ovalbumin or bovine serum albumin, enhancing binding to specific proteins as in the case of RDG-based amino acid sequences (U.S. Pat. Nos. 5,773,412; 5,770,565) used as targeting moieties, or peptides that are known to bind to a wide array of HLA-DR species, such as AKAVAAWTLK AAA (SEQ ID NO: 25 (U.S. App. Pub. No. 2006/0018915) as a DR-targeting moiety. Such modifiers may include moieties which enhance complexation to delivery systems including sustained release delivery systems. Modifiers can be resorbable matrix constructs/synthesizable backbones such as PLGA. Modifiers can be protease resistant moieties such as D-amino acids.

Thus, for any given base peptide sequence, a set of synthesis rules is applied to yield a composition comprising reproducible, consistent mixture of DSPs.

III. Peptide Synthesis Methods

Any known solid phase synthesis appropriate for peptide synthesis may be used to synthesize a composition comprising DSPs, for example as originally described by Merrifield (*J. Am. Chem. Soc.*, 1963, 85:2149) and any variation thereof. More specifically, the synthesis is done in multiple steps by the Solid Phase Peptide Synthesis (SPPS) approach using Fmoc protected amino acids. SPPS is based on sequential addition of protected amino acid derivatives, with side chain protection where appropriate, to a polymeric support (bead). The base-labile Fmoc group is used for N-protection. After removing the protecting group (via piperidine hydrolysis) the next amino acid mixture is added using uranium salts as a coupling reagent (for example, TBTU). After the final amino acid is coupled, the N-terminus is acetylated.

The resulting peptides (attached to the polymeric support through its C-terminus) are cleaved with TFA or TFA cleaving cocktails to yield the crude peptide. During this cleavage step, all of the side chains protecting groups are also cleaved. After precipitation with diisopropyl ether, the solid is filtered and dried. The resulting peptides are analyzed and stored at 8° C. or below.

Additionally, any peptide synthesis method that allows synthesis incorporating more than one amino acid species at a controlled ratio in any given position of the peptide sequence is suitable for use with this invention. Further, as described below, DSPs may be peptidomimetics or include unnatural or modified amino acid, necessitating the adaptation to allow addition of such chemical species to the polymers synthesized up to that point.

The synthesis may include unnatural amino acids, or amino acid analogs. In some embodiments, the DSPs are comprised of naturally occurring and synthetic derivatives, for example, selenocysteine. Amino acids further include amino acid analogs. An amino acid "analog" is a chemically related form of the amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a polypeptide.

The DSPs for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make DSPs of the present invention. The present invention contemplates DSPs containing both D- and L-amino acids, as well as DSPs consisting essentially of either L- or D-amino acids.

In certain embodiments, the DSPs of the present invention include such linear DSPs that are further modified by substituting or appending different chemical moieties. In one embodiment, such modification is at a residue location and in an amount sufficient to inhibit proteolytic degradation of the DSPs in a subject. For example, the amino acid modification may be the presence in the sequence of at least one proline residue; the residue is present in at least one of carboxy- and amino termini; further, the proline can be present within four residues of at least one of the carboxy- and amino-termini. Further, the amino acid modification may be the presence of a D-amino acid.

In certain embodiments, the subject DSPs is a peptidomimetic. Peptidomimetics are compounds based on, or derived from, peptides and proteins. The DSP peptidomimetics of the present invention typically can be obtained by structural modification of one or more native amino acid residues, e.g., using one or more unnatural amino acids, conformational restraints, isosteric replacement, and the like. The subject peptidomimetics constitute the continuum of structural space between peptides and non-peptide synthetic structures.

Such peptidomimetics can have such attributes as being non-hydrolyzable (e.g., increased stability against proteases or other physiological conditions which degrade the corresponding peptide DSPs), increased specificity and/or potency. For illustrative purposes, peptide analogs of the present invention can be generated using, for example, benzodiazepines (e.g., see Freidinger et al. in "Peptides: Chemistry and Biology," G. R. Marshall ed., ESCOM Publisher: Leiden, Netherlands, 1988), substituted gamma lactam rings (Garvey et al. in "Peptides: Chemistry and Biology," G. R. Marshall ed., ESCOM Publisher: Leiden, Netherlands, 1988, p 123), C-7 mimics (Huffman et al. in "Peptides: Chemistry and Biology," G. R. Marshall ed., ESCOM Publisher: Leiden, Netherlands, 1988, p. 105), keto-methylene pseudopeptides (Ewenson et al. *J. Med. Chem.*, 1986, 29:295; and Ewenson et al. in "Peptides: Structure and Function (Proceedings of the 9th American Peptide Symposium)," Pierce Chemical Co. Rockland, Ill., 1985), β-turn dipeptide cores (Nagai et al., *Tetrahedron Lett.*, 1985 26:647; and Sato et al. *J. Chem. Soc. Perkin Trans.*, 1986, 1:1231), β-aminoalcohols (Gordon et al. *Biochem. Biophys. Res. Commun.*, 1985, 126:419; and Dann et al. *Biochem. Biophys. Res. Commun.*, 1986, 134:71), diaminoketones (Natarajan et al. *Biochem. Biophys. Res. Commun.*, 1984, 124:141), and methyleneamino-modified (Roark et al. in "Peptides: Chemistry and Biology," G. R. Marshall ed., ESCOM Publisher: Leiden, Netherlands, 1988, p 134). Also, see generally, Session III: Analytic and synthetic methods, in "Peptides: Chemistry and Biology," G. R. Marshall ed., ESCOM Publisher: Leiden, Netherlands, 1988.

The molecular weight of a DSP composition can be adjusted during polypeptide synthesis or after the DSPs have been synthesized. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the DSPs with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In one particular embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

In certain embodiments, DSP is modified after synthesis. Such modification is useful, for instance, to create DSP to direct the subsequent antibody response to features of the DSP that have application in either a research, diagnostic, or therapeutic context. Examples of post-synthesis modifications include but are not limited to sugars such as glycogen, galactose, glucose, modified sugars such as sialic acid-galactose or its derivatives, (sialic acid=5-amino-3,5-dideoxy-D-glycero-D-galacto-nonulosonic acid) or alternative amino acids such as citrulline. More specific examples of modification by sugars are sialic acid-α2,3-galactose linkage and sialic acid-α2,6-galactose linkage, which is known to affect antigenicity of the epitope. (Suzuki et al, *J. Virol.* 2000, 74(24): 11825-11831. In one embodiment, the post-synthesis modification is performed using enzymes. In another embodiment, the post-synthesis modification is performed manually using chemical complexation techniques well known in the prior art.

A further embodiment of the instant invention is the use of specific glycosilated/glycogenated forms of a DSP to create antibodies against such a form of a ligand. In one embodiment the ligand itself is a viral coat protein. In another embodiment the ligand itself is an antibody. In one embodiment of the instant invention, the post-translational modification of a DSP is performed using glycogen synthase, or alternatively using chemical complexation techniques well known in the art.

IV. Pharmaceutical Composition

One aspect of the present invention is a pharmaceutical composition comprising a DSP composition. As described below in the method of treatment as an aspect of this invention, the DSP composition produced by the process of the invention is useful in preventing infectious diseases by acting as vaccines.

The DSPs of the present invention may be administered to the subject as a composition which comprises a pharmaceutically effective amount of DSPs and an acceptable carrier and/or excipients. A pharmaceutically acceptable carrier includes any solvents, dispersion media, or coatings that are physiologically compatible. Preferably, the carrier is suitable for oral, rectal, transmucosal (including by inhalation), parenteral, intravenous, intramuscular, intraperitoneal, intradermal, transdermal, topical, or subcutaneous administration. One exemplary pharmaceutically acceptable carrier is physiological saline. Other pharmaceutically acceptable carriers and their formulations are well-known and generally described in, for example, *Remington's Pharmaceutical Science* (18$^{th}$ Ed., ed. Gennaro, Mack Publishing Co., Easton, Pa., 1990). Various pharmaceutically acceptable excipients are well-known in the art and can be found in, for example, *Handbook of Pharmaceutical Excipients* (4$^{th}$ ed., Ed. Rowe et al. Pharmaceutical Press, Washington, D.C.). The composition can be formulated as a solution, microemulsion, liposome, capsule, tablet, or other suitable forms. The active component which comprises the copolymer may be coated in a material to protect it from inactivation by the environment prior to reaching the target site of action. The pharmaceutical compositions of the present invention are preferably sterile and non-pyrogenic at the time of delivery, and are preferably stable under the conditions of manufacture and storage. When desirable, the composition further comprises components to enhance stability, permeability, and/or bioavailability, such as particulate forms protective coatings, protease inhibitors or permeation enhancers for various routes of administration, including parenteral, pulmonary, nasal and oral.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pre-gelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well-known in the art.

In one embodiment, the oral composition is enterically-coated. Use of enteric coatings is well known in the art. For example, Lehman (1971) teaches enteric coatings such as Eudragit S and Eudragit L. The Handbook of Pharmaceutical Excipients, 2$^{nd}$ Ed., also teaches Eudragit S and Eudragit L applications. One Eudragit which may be used in the present invention is L30D55. Preparations for oral administration may be suitably formulated to give controlled release of the active compound.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compositions may be formulated for administration by injection, e.g., by bolus injection or continuous infusion in a parenteral, intravenous, intraperitoneal, intramuscular, or subcutaneous manner. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile pyrogen free water, before use.

In a preferred embodiment, compositions comprising DSP compositions are formulated in accordance with routine procedures as pharmaceutical compositions adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline, with the intervals between administrations being greater than 24 hours, 32 hours, or more preferably greater than 36 or 48 hours. Where the composition is administered by injection, an ampoule of sterile water or saline for injection can be provided so that the ingredients may be mixed prior to administration.

In other embodiments of the present invention, the pharmaceutical compositions are regulated-release or sustained release formulations. DSP compositions of the present invention may be admixed with biologically compatible polymers or matrices which control the release rate of the copolymers into the immediate environment. Controlled or sustained release compositions include formulation in lipophilic depots (e.g., fatty acids, waxes, oils). One embodiment of sustained release formulations is transdermal patches.

In some embodiments of the present invention, pharmaceutical compositions comprise DSPs formulated with oil and emulsifier to form water-in-oil microparticles and/or emulsions. The oil may be any non-toxic hydrophobic material liquid at ambient temperature to about body temperature, such as edible vegetable oils including safflower oil, soybean oil, corn oil, and canola oil; or mineral oil.

Chemically defined oil substance such as lauryl glycol may also be used. The emulsifier useful for this embodiment includes Span 20 (sorbitan monolaurate) and phosphatidylcholine. In some embodiments, a DSP composition is prepared as an aqueous solution and is prepared into an water-in-oil emulsion dispersed in 95 to 65% oil such as mineral oil, and 5 to 35% emulsifier such as Span 20. In another embodiment of the invention, the emulsion is formed with alum rather than with oil and emulsifier. These emulsions and microparticles reduce the speed of uptake of DSPs, and achieve controlled delivery.

In another embodiment, the controlled and/or sustained delivery is achieved by implantable medical devices coated with sustained-release formulations, or implantable pharmaceutical formulation suitable for sustained-release of the active components.

In some embodiments of the invention, pharmaceutical compositions comprise a set of nucleic acid vectors encoding a DSP composition, which is expressed as polypeptides within a subject. The vectors may comprise transcription- and/or translation-controlling elements such that the timing and level of the DSPs composition produced may be regulated.

In some embodiments, the vectors also comprise one or more additional coding sequences, which encodes a therapeutically beneficial polypeptide or a second, different composition of DSPs that is not a member of the first DSP composition. In alternative embodiments, a pharmaceutical composition comprises one or more vectors, each encoding either: the DNA sequences for the DSPs of a first DSP composition, or the DNA sequences for the DSPs of a second DSPs composition or a therapeutically beneficial polypeptide, that is not a member of the first DSP composition. Such therapeutically beneficial polypeptide may be, for example, an immunomodulatory cytokine or a growth factor.

Some embodiments of the invention are pharmaceutical compositions for targeted delivery of the DSP composition of the invention. In such embodiments, a pharmaceutical composition comprises a DSP composition that is complexed with a targeting moiety. The targeting moiety allows localized delivery of the DSP composition to a desired location or microenvironment within the subject. A targeting moiety include, and may be selected from, the group comprising a chemical group or functionality such as biotin or simple sugars, a single or double stranded DNA sequence of various lengths, a single or double stranded RNA sequence of various lengths, a peptide of various lengths, an antibody including single chain antibodies, Fab', or modified antibodies, a lipid, or a glycolipid. More than one of such moiety may be used at the same time in combination. For examples of targeting moieties, see U.S. Pat. No. 6,268,488; U.S. Appl. Pub. No. 2003/0190676; and see, for example, www.covx.com/tech_creating.html.

In one embodiment of the invention, the complex has characteristics of a prodrug, causing the DSP composition to exhibit no pharmaceutical activity of the present invention until the dissolution of the complex in the subject. In another embodiment, the complex does not affect the activity of the DSP composition.

Any methods generally known to one skilled in the art may be used to produce a complex of the instant invention and a targeting moiety. The target moiety may be complexed to the DSPs by a chemical bond, which may be covalent, ionic, hydrophobic, or van der Waals force, directly or through another chemical entity. Alternatively, the target moiety may be co-localized with the DSPs through common medium such as a biocompatible resin within which the DSP composition is included. The manner of forming a complex is chosen also based on the active state of the instant invention while existing in the combination and whether a permanent complex or a transitory complex is desired.

In some embodiments, the pharmaceutical compositions also include additional therapeutically active agents. Such additional ingredient can be one or more of: an additional DSP composition that binds to a different target, an antibody which activates inflammatory molecules, or cytokines. Further additional ingredient can be activating cytokines and chemokines (as described in Shaw, Jennifer, *Infection and Immunity* 2001, 69:4667-4672) taken from the group consisting of Mip1β, Mip1α, Mip-2, Mip3α, IP-10, MCP-1, TCA-3, IL-1, IL-18, IL-6, IFNγ, MIF, IL-12, CCR7.

Further, a form of vitamin D that is or becomes biologically active within the body of the subject receiving such form of vitamin D may also be used as an additional ingredient. The two main forms of vitamin D are: vitamin D3 or cholecalciferol, which is formed in the skin after exposure to sunlight or ultraviolet light, and ergocalciferol or vitamin D2 which is obtained by irradiation of plants or plant materials or foods. The differences are situated in the side chain. Vitamin D3 may be obtained from natural sources such as fatty fish such as herring and mackerel. In the body, two other forms of vitamin D3 can be found. Vitamin D3 is hydroxylated in the liver into 25-hydroxyvitamin D3 (25(OH)D), and subsequently in the kidney into 1,25-dihydroxyvitamin D3 (1,25(OH)2D), which is the active metabolite that stimulates the calcium absorption from the gut (Feldman et al., 2005). When 1,25(OH)2D is sufficiently available, 24,25-dihydroxyvitamin D (24,25 (OH)2D) is formed in the kidney, which is further catabolized.

Another class of therapeutically active agents useful as an additional agent is immune boosters which increases the production of common lymphoid precursors (CLPs) from the multilineage potential cells. An example of such agent is PBI-1402 developed by ProMetic in Quebec, Canada.

The invention further provides a kit comprising (i) a composition comprising a DSP composition or DNA delivery vehicle comprising DNA encoding DSPs and (ii) instructions for administering the composition to a subject in need thereof at intervals greater than 24 hours, more preferably greater than 36 hours, for the treatment of a disease, such as an infection with an invading pathogen. In one embodiment, the invading pathogen is a virus. In a preferred embodiment, the virus is influenza. In a preferred embodiment, the DSP composition is formulated in dosages for administration of greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any intervening interval thereof. In another embodiment of the kits described herein, the instructions indicate that the DSP is to be administered every about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any interval in between. Kits may comprise additional components, such as packaging, instructions, and one or more apparatuses for the administration of the copolymer, such as a hypodermic syringe V. Methods of Treatment The instant invention provides for a further improvement on the need to improve the effectiveness of vaccines. The improvement takes form in an ability to dynamically administer the compound based on the ability of the compound to achieve an increased immune activation, while generating either a $T_H1$ immune posture, or a $T_H2$ immune posture, and while producing anti-compound antibodies at either a low or a high level. Dynamic administration of random sequence copolymer is comprised of any combination of dose, regimen, route of administration, and/or formulation. This dynamic immunomodulation provides for increased effectiveness at any of the multiple stages of a disease within a particular patient, as well as the ability to treat multiple, pathogenic antigenic-determinant unrelated diseases more effectively.

The invention provides methods for the treatment of a disease or prevention of further progression of a disease (including a disease in its latent stage) in a subject, preferably in a human, which subject is afflicted with or is suspected to be afflicted with the disease. Another embodiment of the present invention is a method for prophylactically treating a subject at risk of developing e.g., an infectious disease by administering a DSP composition. A subject at risk is identified by, for example, determining the genetic susceptibility to an infectious disease by testing for alleles of HLA, and/or based on familial history, geographic location, economic or social situations, or genetic markers.

A particular aspect of the invention is a method of protecting a subject from an influenza infection wherein the influenza virus is a new immunologic subtype comprising the step of administering a pharmaceutical composition comprising a DSP composition the base sequence of which comprises an epitope from hemagglutinin of an influenza virus subtype that caused the most immediate past epidemic at any given time when such protection is desired. Such new subtype may occur either by antigenic drift or antigenic shift. By the most immediate past epidemic, it is meant that, at any given time when such protection is desired, there would have been the last infectious event that infected a large number of people. The DSPs of the invention that would be created using the region of HA from such most immediate past epidemic, which region corresponds to SEQ ID NO: 6 or 7 and contains epitopes, are expected to be particularly effective in conferring immunity to the next flu surge, whether it is a simple antigenic drift or it is a major antigenic shift. This is because there is immunological overlap between two temporally adjacent flu epidemics, and expansion of immunoloreactivity that the DSPs induces can be expected to confer adequate protection to a new influenza subtype that would otherwise be recognized as a new and unknown antigen.

One aspect of the invention provides methods of treating or preventing a disease, the method comprising administering to said subject a dosing regimen of an effective amount of a DSP composition for the protection against infection by an invading pathogen treatable with the DSP composition, said effective amount delivered to said subject once, twice, or multiple times at time intervals greater than 24 hours, 36 hours, or more preferably greater than 48 hours. A DSP composition may be administered more than once as a booster dose. A related aspect of the invention provides a method for the treatment of a subject in need thereof, comprising administering to said subject a dosing regimen of an effective amount of a DSP composition for the amelioration of a disease treatable with the DSP composition, said effective amount delivered to the subject using a sustained-release formulation which administers the DSP composition over a period of at least 2 days, at least 4 days, or at least 6 days, at least 10 days, or at least 14 days, or at least 28 days, wherein the effective amount is an amount that is effective if delivered daily.

One aspect of the invention is the administration of a DSP composition to a subject in need thereof, as described above, in combination with other therapeutic agents that are effective in treating the conditions that are treated by administration of the DSP, or conditions that accompany or occur concurrently with the conditions that are treated by administration of the DSP. The additional therapeutically active agents may treat the same or related disease as the DSP composition, or may be intended to treat an undesirable side effect of administration of the DSP composition, such as to reduce swelling at a site of intradermal injection. Alternatively, the other therapeutic agents enhance the activity of DSP compositions. Such additional therapeutic agents are, by way of example, antibodies, cytokines, growth factors, enzyme inhibitors, antibiotics, antiviral agents, anti-inflammatory including steroids, immune boosters, antimetabolites, soluble cytokine receptors, and vitamin D or agents that increase the level of circulating vitamin D, toll-like receptor agonists, CpG oligodeoxynucleotides, surface charged poly(lactide-co-glycolide) microparticles, any of the above encapsulated into liposomes, archaeosome adjuvants, mucosal adjuvants, polyphosphazenes. Adjuvants may include aluminium hydroxide, aluminium phosphate and calcium phosphate, other adjuvants based on oil emulsions, products from bacteria (their synthetic derivatives as well as liposomes) or non-infectious gram-negative bacteria, endotoxins, cholesterol, fatty acids, aliphatic amines, paraffinic and vegetable oils, monophosphoryl lipid A, ISCOMs with Quil-A, and Syntex adjuvant formulations (SAFs) containing the threonyl derivative or muramyl dipeptide, or toll-like receptor antagonists or agonists. Additional therapeutically active agents also include copolymers which bind to a HLA molecule associated with the disease such as Copolymer-1, or another DSP composition. The HLA molecule may be an HLA-DQ molecule or an HLA-DR molecule. The enzyme inhibitor may be a protease inhibitor or a cyclooxygenase inhibitor. Examples of the therapeutically active agents to be administered in conjunction with the DSP composition are recited in Section IV, "Pharmaceutical Composition" section, though the administration of these agents are not limited to co-administration as a single composition. The additional therapeutic agents may be administered before, concomitantly with, or after the administration of the DSP composition, at such time that the effect of the additional therapeutic agents and the effect of the DSP composition overlap at some time point.

In one embodiment of the methods described herein, the route of administration can be oral, intraperitoneal, transdermal, subcutaneous, by intravenous or intramuscular injection, by inhalation, topical, intralesional, or by infusion; liposome-mediated delivery; buccal, intrathecal, gingival pocket, rectal, intravaginal, intrabronchial, nasal, transmucosal, intestinal, ocular or otic delivery, or any other methods known in the art as one skilled in the art may easily perceive. Administration can be systemic or local. In the event more than one DSP composition is being administered to a subject during the same or overlapping time period, such additional therapeutic agent may be administered by a route different from that for the administration of the DSP composition.

In general, an embodiment of the invention is a method of administering a suitable dose of a therapeutic DSP composition that will be the lowest effective dose to produce a therapeutic effect, for example, mitigating symptoms. The therapeutic DSP compositions are preferably administered at a dose per subject, which corresponds to a dose per day of at least about 0.0001 mg, at least about 0.002 mg, at least about 0.02 mg, at least about 0.2 mg, at least about 2 mg, or at least about 10 mg as appropriate minimal starting dosages, or about x mg, wherein x is one thousandth of an integer between 1 and 20. In one embodiment of the methods described herein, a dose of about 0.0001 to about 500 mg/kg, can be administered. In general, the effective dosage of the DSP composition of the present invention is from about 0.050 to about 400 micrograms of the composition per kilogram (i.e. 0.00005 to 0.4 mg/kg) of the subject per day, and more specifically, 0.001 to 0.01 mg/kg of the subject per day. In one specific embodiment, the equivalent dosage per day, regardless of the frequency with which the doses are administered, is from about 0.05 to 100, or more specifically, from about 0.10 to 40, or from about 1 to 20, or more specifically about 2.0 mg/day. In another specific embodiment, each individual dosage in the treatment regimen is from about 0.0001 to 100 mg, more specifically a dose of about 0.001 to 1 mg, more specifically a dose of about 0.001 to 0.01 mg per dose. In certain embodiments, total dosage per day is and total dose per day. In another specific embodiment, the dosage is determined in relation to the body surface area of a subject. In general, the effective dosage of the DSP composition is from about 0.05 to 100 microgram/m$^2$, more specifically from about 0.10 to 50, or more specifically from about 0.38 to 38 microgram/m$^2$ of the body surface area of a subject.

However, it is understood by one skilled in the art that the dose of the DSP composition of the invention will vary depending on the subject and upon the particular route of administration used. It is routine in the art to adjust the dosage to suit the individual subjects. Additionally, the effective amount may be based upon, among other things, the size of the DSPs, the biodegradability of the DSPs, the bioactivity of the DSPs and the bioavailability of the DSPs. If the DSPs does not degrade quickly, such as is expected when the DSPs comprise unnatural amino acids or are peptidomimetics, is bioavailable and highly active, a smaller amount will be required to be effective. The actual dosage suitable for a subject can easily be determined as a routine practice by one skilled in the art, for example a physician or a veterinarian given a general starting point. For example, the physician or veterinarian could start doses of the DSP composition of the invention employed in the pharmaceutical composition at a level lower than that required in order to achieve the desired therapeutic effect, and increase the dosage with time until the desired effect is achieved. The dosage of the DSP composition may either be increased in the event the patient does not respond significantly to current dosage levels, or the dose may be decreased if an alleviation of the symptoms of the disorder or disease state is observed, or if the disorder or disease state has been ablated, or if an unacceptable side effects are seen with the starting dosage.

In one embodiment, a therapeutically effective amount of the DSP composition is administered to the subject in a treatment regimen comprising intervals of at least 36 hours, or more preferably 48 hours, between dosages. In another embodiment, the DSP composition is administered at intervals of at least 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days. In some embodiments, the DSP composition is administered every other day, while in other embodiments it is administered weekly. If two different DSP compositions, or DSP composition with another therapeutic agent, are administered to the subject, such administration may take place at the same time, such as simultaneously, or essentially at the same time, such as in succession. Alternatively, their administration may be staggered. For example, two DSP compositions which are each administered every 48 hours may both be administered on the same days, or one may be administered one day and the other on the next day and so on in an alternating fashion.

In other embodiments, the DSP composition is administered in a treatment regimen which comprises at least one uneven time interval, wherein at least one of the time intervals is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days.

In one embodiment, the DSP composition is administered to the subject once. In one embodiment, the DSP composition is administered to the subject at least twice during a treatment regimen. Accordingly, in one embodiment, at least one of the time intervals between administrations is greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours.

In another embodiment, the dosage regimen consists of two or more different interval sets. For example, a first part of the dosage regimen is administered to a subject daily, every other day, or every third day, for example, at about 22 mg copolymer/m$^2$ body surface area of the subject, wherein the subject is a human. In some embodiment of the invention, the dosing regimen starts with dosing the subject every other day, every third day, weekly, biweekly, or monthly. The dosage for administration every other day or every third day may be up to about 65 mg/m$^2$ and 110 mg/m$^2$ respectively. For a dosing regimen comprising dosing of the random copolymer every week, the dose comprises up to about 500 mg/m$^2$, and for a dosing regimen comprising dosing of the random copolymer every two weeks or every month, up to 1.5 g/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

In other embodiments of the invention, any of the methods of the invention may be practiced using sustained release formulation comprising a DSP composition. When administering a DSP composition of the invention using a sustained release formula, the overall exposure to the DSP is generally lower than in bolus administration. For example, a first part of the dosage regimen is administered to a subject daily, every other day, or every third day, for example, at about 22 mg DSP/m$^2$ body surface area of the subject per dose, wherein the subject is a human. In some embodiment of the invention, the dosing regimen uses sustained release formula, dosing the subject every other day, every third day, weekly, biweekly, or monthly so that the copolymer is released during the interval. The dosage for administration every other day or every third day may be up to about 35 mg/m² and 65 mg/m² per dose, respectively. For a dosing regimen comprising dosing of the DSP composition every week, the dose comprises up to about 140 mg/m² per dose, and for a dosing regimen comprising dosing of the DSP composition every two weeks or every month, up to 750 mg/m² may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 140 mg/m² body surface area weekly, up to maximum of about 1.5 g/m² body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m² body surface area weekly. If, during the step-down dosage regimen, the disease condition relapses, the first dosage regimen may be resumed until effect is seen, and the second dosing regimen may be implemented. This cycle may be repeated multiple times as necessary.

For such sustained release administration, such method comprises applying a sustained-release transdermal patch or implanting a sustained-release capsule or a coated implantable medical device so that a therapeutically effective dose of the copolymer of the present invention is delivered at defined time intervals to a subject of such a method. The DSP composition of the subject invention may be delivered via a capsule which allows regulated-release of the DSPs over a period of time. Controlled or sustained-release compositions include formulation in lipophilic depots (e.g., fatty acids, waxes, oils). Also comprehended by the invention are particulate compositions coated with polymers (e.g., poloxamers or poloxamines). In certain embodiments, a source of a DSP composition is stereotactically provided within or proximate to the area of pathogenic attack.

An improvement in the symptoms of a subject afflicted with a disease as a result of administration of the DSP composition may be noted by a decrease in frequency of recurrences of episodes of the disease symptoms, by decrease in severity of symptoms, and by elimination of recurrent episodes for a period of time after the start of administration. A therapeutically effective dosage preferably reduces symptoms and frequency of recurrences by at least about 20%, for example, by at least about 40%, by at least about 60%, and by at least about 80%, or by about 100% elimination of one or more symptoms, or elimination of recurrences of the autoimmune disease, relative to untreated subjects. The period of time can be at least about one month, at least about six months, or at least about one year.

DEFINITIONS

The term "associated with" means "coexistent with" or "in correlation with." The term does not necessarily indicate causal relationship, though such relationship may exist.

The term "binding" refers to a direct association between two molecules, due to, for example, covalent, electrostatic, hydrophobic, ionic and/or hydrogen-bond interactions under physiological conditions, and including interactions such as salt bridges and water bridges.

The term "HLA molecule" means any class II major histocompatibility complex glycoproteins.

The term "immunomodulation" means the process of increasing or decreasing the immune system's ability to mount a response against a particular antigenic determinant through the T-cell receptor ("TCR")'s recognition of complexes formed by major histocompatibility complex ("MHC") and antigens.

The term "patient" refers to an animal, preferably a mammal, including humans as well as livestock and other veterinary subjects.

The terms "peptide", "polypeptide" and "protein" are used interchangeably herein. These terms refer to unmodified amino acid chains, and also include minor modifications, such as phosphorylations, glycosylations and lipid modifications. The terms "peptide" and "peptidomimetic" are not mutually exclusive and include substantial overlap.

A "peptidomimetic" includes any modified form of an amino acid chain, such as a phosphorylation, capping, fatty acid modification and including unnatural backbone and/or side chain structures. As described below, a peptidomimetic comprises the structural continuum between an amino acid chain and a non-peptide small molecule. Peptidomimetics generally retain a recognizable peptide-like polymer unit structure. Thus, a peptidomimetic may retain the function of binding to a HLA protein forming a complex which activates autoreactive T cells in a patient suffering from an autoimmune disease.

The term "amino acid residue" is known in the art. In general the abbreviations used herein for designating the amino acids and the protective groups are based on recommendations of the IUPAC-IUB Commission on Biochemical Nomenclature (see *Biochemistry* (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Most of the amino acids used in the DSPs of the present invention may exist in particular geometric or stereoisomeric forms. In preferred embodiments, the amino acids used to form the subject DSPs are (L)-isomers, although (D)-isomers may be included in the DSPs such as at non-anchor positions or in the case of peptidomimetic versions of the DSPs.

"Prevent", as used herein, means to measurably delay or preclude the onset of, for example, one or more symptoms, of a disorder or condition.

"Treat", as used herein, means at least lessening the severity or ameliorating the effects of, for example, one or more symptoms, of a disorder or condition.

"Treatment regimen" as used herein, encompasses therapeutic, palliative and prophylactic modalities of administration of one or more compositions comprising one or more DSP compositions. A particular treatment regimen may last for a period of time at a particular dosing pattern, which will vary depending upon the nature of the particular disease or disorder, its severity and the overall condition of the patient, and may extend from once daily, or more preferably once every 36 hours or 48 hours or longer, to once every month or several months.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999; and PCR Protocols, ed. by Bartlett et al., Humana Press, 2003; PHARMACOLOGY A Pathophysiologic Approach Edited by Josehp T. DiPiro, Robert Talbert, Gary, Yee, Gary Matzke, Barbara Wells, and L. Michael Posey. 5th edition 2002 McGraw Hill; Pathologic Basis of Disease. Ramzi Cotran, Vinay Kumar, Tucker Collins. 6th Edition 1999. Saunders.

Example 1

Preparation of a DSP Composition from Fictitious Base Peptides

For ease of understanding, as an illustration, preparation of a DSP composition deriving from two fictitious peptide sequences, representing a known epitope, is described and shown in the table depicted in FIG. 6. In this illustration, the cassettes consist of five amino acids each, (×1, ×2, ×3, ×4, ×5=THMCE in $y_1$ and PWKNA in $y_2$). THMCE is defined as having an input ratio of a=7, b=1, c=1, d=1, e=10. PWKNA is defined as having an input ratio of a=1, b=3, c=3, d=3, e=20. For synthesis, the identity of group of amino acids occupying each amino acid position for each peptide is determined using the preferred method of amino acid substitution described by Kosiol et al., J. Theoretical Biol. 228:97-106, 2004, as shown in FIG. 4 (or less preferably an equivalent means of systematically altering amino acids), and the overall ratio of amino acids that occupy each of such positions in the resulting collective DSP composition is given above. Each cassette, $y_1$ and $y_2$, will twice be repeated two times, generating an order of $y_1\ y_1\ y_2\ y_2\ y_1\ y_1\ y_2\ y_2$. $N_n$ are the number of times the sequence within the cassette is to be repeated, and in our fictitious example N=2. MN can be any type of modifying moiety. MN must be amenable to solid phase synthesis methods. For this fictitious example, a modifying moiety of amino acids that would target the DSP to a certain location within a subject is chosen, such as an RGD-based sequence motif on a particular integrin such as alphaVbeta3. In this example the C-terminal modifier will also be an RGD-based motif, but comprised of D-amino acids.

The DSP composition as described above is prepared using a solid phase peptide synthesis method as described elsewhere in this disclosure.

Example 2

Preparation of a DSP Composition from Influenza Hemagglutinin Epitope as a Source Peptide As a starting point, a hemagglutinin sequence of a strain of influenza A subtype H5N1 avian flu virus isolated from an infected human, A/Egret/Egypt/1162/NAMRU-3/06, is chosen (Steven J et al., J Mol Biol, 2008 381:1382-94). The ascension number, ACD62257, and sequence, SEQ ID No: 15, is found using the database: http://www.ncbi.nlm.nih.gov/genomes/FLU/Database/multiple.cgi. A 3D protein structure is created using RasMol (http://rasmol.org/), or an equivalent, after obtaining a model using ModBase (*Nucleic Acids Research* 34, D291-D295, 2006), or an equivalent comparative modeling database. A BLAST search is performed, (http://www.ncbi.nlm.nih.gov/sutils/blast_table.cgi?taxid=11308&selectall), using the advanced BLAST to retrieve a maximum number of sequences, in order to identify homologous influenza A, B, or C variants. A phylogenic tree is created using fast minimum evolution, 0.85 maximum sequence Grishin difference. The leading node in the tree is selected to obtain an alignment of the entire tree. The alignment is analyzed for mutations in amino acids between the different flu variants obtained in the search in order to obtain rules for amino acid substitution. A summary of the mutations is made in order to determine the pattern and frequency of mutations at each amino acid position. The mutation patterns are coded into RasMol so that the identification of variable regions in the context of the 3D structure of the viral protein. The ACD62257 HA aa 115-163 sequence is shown below as row 1. Based on the variant identification, analysis and summary, amino acids are chosen and placed into rows 2 through 6, with row 7 always being Alanine. An exemplary percentage of how to mix these amino acids in a peptide synthesis procedure is shown in the subsequent rows. The methods and rules to define the identity of amino acids for each position of the resulting peptides are described above in Example 1. As with Example 1, the DSP composition is synthesized using a solid phase peptide synthesis method. The following tables disclose SEQ ID NO: 26 in the line designated as "1" under the caption "Amino Acids."

| Position | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Amino Acids | | | | | | | | | | | | | | | | | |
| 1 | C | I | I | P | K | S | S | W | S | D | H | E | A | S | S | G | V |
| 2 | | | | | | | | P | S | S | | D | | | L | | |
| 3 | | | | | | | | | N | | | | | | | | |
| 4 | | | | | | | | | | | | | | | | | |
| 5 | | | | | | | | | | | | | | | | | |
| 6 | | | | | | | | | | | | | | | | | |
| 7 | | A | A | A | A | A | A | A | A | A | A | A | | A | A | | |
| Percentage | | | | | | | | | | | | | | | | | |
| 1 | 100 | 70 | 70 | 70 | 70 | 70 | 70 | 70 | 70 | 40 | 90 | 65 | 100 | 90 | 65 | 100 | 100 |
| 2 | | | | | | | | 20 | 20 | 20 | | 25 | | | 25 | | |
| 3 | | | | | | | | | | 30 | | | | | | | |
| 4 | | | | | | | | | | | | | | | | | |
| 5 | | | | | | | | | | | | | | | | | |
| 6 | | | | | | | | | | | | | | | | | |
| 7 | | 30 | 30 | 30 | 30 | 30 | 30 | 10 | 10 | 10 | 10 | 10 | | 10 | 10 | | |
| TOTAL | 100 | 100 | 100 | 100 | 100 | 100 | 100 | 100 | 100 | 100 | 100 | 100 | 100 | 100 | 100 | 100 | 100 |

| Position | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|
| Amino Acids | | | | | | | | | | | | | | | | | |
| 1 | S | S | A | C | P | Y | Q | G | R | S | S | F | F | R | N | V | V |
| 2 | | A | | | | | H | | K | P | | | Y | | | | |
| 3 | | | | | | | N | | S | | | | | | | | |
| 4 | | | | | | | L | | V | | | | | | | | |
| 5 | | | | | | | | | T | | | | | | | | |
| 6 | | | | | | | | | G | | | | | | | | |
| 7 | | | | A | | | A | A | A | A | | | | | | | |
| Percentage | | | | | | | | | | | | | | | | | |
| 1 | 100 | 100 | 100 | | 100 | 100 | 40 | 90 | 20 | 45 | 100 | 100 | 100 | 100 | 100 | 100 | 100 |
| 2 | | | | | | | 30 | | 15 | 45 | | | | | | | |
| 3 | | | | | | | 20 | | 15 | | | | | | | | |
| 4 | | | | | | | | | 15 | | | | | | | | |
| 5 | | | | | | | | | 15 | | | | | | | | |
| 6 | | | | | | | | | 10 | | | | | | | | |
| 7 | | | | 100 | | | 10 | 10 | 10 | 10 | | | | | | | |
| TOTAL | 100 | 100 | 100 | 100 | 100 | 100 | 100 | 100 | 100 | 100 | 100 | 100 | 100 | 100 | 100 | 100 | 100 |

| Position | 35 | 36 | 37 | 38 | 39 | 40 | 41 | 42 | 43 | 44 | 45 | 46 | 47 | 48 | 49 | 50 | 51 |
|---|---|---|---|---|---|---|---|---|---|---|---|---|---|---|---|---|---|
| Amino Acids | | | | | | | | | | | | | | | | | |
| 1 | W | L | I | K | K | D | N | A | Y | P | T | I | K | R | S | Y | C |
| 2 | | | T | T | R | N | S | T | | | | | | K | | | |
| 3 | | | V | E | | | D | S | | | | | | | | | |
| 4 | | | | | | | | | | | | | | | | | |
| 5 | | | | | | | | | | | | | | | | | |
| 6 | | | | | | | | | | | | | | | | | |
| 7 | | | | A | A | A | A | A | | | | | | | | | |
| Percentage | | | | | | | | | | | | | | | | | |
| 1 | 100 | 100 | 70 | 70 | 80 | 45 | 40 | 40 | 100 | 100 | 100 | 100 | 100 | 60 | 100 | 100 | 100 |
| 2 | | | 10 | 10 | 10 | 45 | 40 | 40 | | | | | | 40 | | | |
| 3 | | | 10 | 10 | | | 10 | 20 | | | | | | | | | |
| 4 | | | | | | | | | | | | | | | | | |
| 5 | | | | | | | | | | | | | | | | | |
| 6 | | | | | | | | | | | | | | | | | |
| 7 | | | 10 | 10 | 10 | 10 | 10 | | | | | | | | | | |
| TOTAL | 100 | 100 | 100 | 100 | 100 | 100 | 100 | 100 | 100 | 100 | 100 | 100 | 100 | 100 | 100 | 100 | 100 |

Once formulated into a pharmaceutically acceptable preparation, the DSP is administered to a subject in need of immune protection against the drift-variants associated with the A/Egret/Egypt/1162/NAMRU-3/06 cluster. The DSP directs the subject's immune response to all of the variants within the cluster, thus anticipating multiple directions the transition, or shift, from one cluster to another more virulent cluster will take (Smith D J et al., Science 305:371-6, 2004). Once the new dominant shifted variants are identified through the Global Surveillance network, or equivalent, a new H5N1 HA-based DSP polymer is designed, manufactured and administered using the above methods.

It can be easily discerned by one skilled in the art that the above example is repeatable with subsequent strains of H5N1, with other serological variants or with other viral proteins selected from the group consisting of CMV glycoproteins B, H, and gCIII, HIV-1 envelope, glycoproteins, RSV envelope glycoproteins, HSV envelope glycoproteins, EBV envelope glycoproteins, VZV envelope glycoproteins, HPV envelope glycoproteins, Hepatitis family surface antigens The following references are exemplary sources of epitopes useful as base peptide sequences
Diamond, D. et al., *Blood* 90:1751-57 (1997) 1
Belyakov, I., *Proc. Nat. Acad. Sci. USA*, 95:1709 (1998) 2
Saad, M. D., et al., direct submission to GenBank, ACD62257 3 Viral and Zoonotic Diseases Research Program, U.S. Naval Medical Research Unit No. 3, Extension of Ramses Street, Nasr City, Cairo 11517, Egypt Mase, M., et al., "Characterization of H5N1 influenza A viruses 4 isolated during the 2003-2004 influenza outbreaks in Japan", Virology 332 (1), 167-176 (2005)
Kaverin, N. V. et al., "Structure of antigenic sites on the 5 hemagglutinin molecule of H5 avian influenza virus and phenotypic variation of escape mutants," J. Gen. Virol. 83: 2497-2505 (2002)

The contents of any patents, patent applications, patent publications, or scientific articles referenced anywhere in this application are herein incorporated in their entirety.

Sequence Listings in Addition to Table I

```
HEMAGGLUTININ INFLUENZA A VIRUS (A/BRISBANE/59/2007(H1N1)) ACCESSION
CA28844
                                                        SEQ ID NO: 8
MKVKLLVLLC TFTATYADTI CIGYHANNST DTVDTVLEKN VTVTHSVNLL ENSHNGKLCL

LKGIAPLQLG NCSVAGWILG NPECELLISK ESWSYIVEKP NPENGTCYPG HFADYEELRE

QLSSVSSFER FEIFPKESSW PNHTVTGVSA SCSHNGESSF YRNLLWLTGK NGLYPNLSKS

YANNKEKEVL VLWGVHHPPN IGDQKALYHT ENAYVSVVSS HYSRKFTPEI AKRPKVRDQE

GRINYYWTLL EPGDTIIFEA NGNLIAPRYA FALSRGFGSG IINSNAPMDK CDAKCQTPQG

AINSSLPFQN VHPVTIGECP KYVRSAKLRM VTGLRNIPSI QSRGLFGAIA GFIEGGWTGM

VDGWYGYHHQ NEQGSGYAAD QKSTQNAING ITNKVNSVIE KMNTQFTAVG KEFNKLERRM

ENLNKKVDDG FIDIWTYNAE LLVLLENERT LDFHDSNVKN LYEKVKSQLK NNAKEIGNGC

FEFYHKCNDE CMESVKNGTY DYPKYSEESK LNREKIDGVK LESMGVYQIL AIYSTVASSL

VLLVSLGAIS FWMCSNGSLQ CRICI

HEMAGGLUTININ [INFLUENZA A VIRUS (A/SOUTH AUSTRALIA/55/2005(H1N1)
ACCESSION ABJ16653
                                                        SEQ ID NO: 9
MKVKLLVLLC TFTATYADTI CIGYHANNST DTVDTVLEKN VTVTHSVNLL EGSHNGKLCL

LKGIAPLQLG NCSVAGWILG NPECELLISK ESWSYIVETP NPENGTCYPG YFADYEELRE

QLSSVSSFER FEIFPKESSW PNHTVTGVSA SCSHNGKSSF YRNLLWLTGK NGLYPNLSKS

YANNKEKEVL VLWGVHHPPN IGBQRALYHT ENAYVSVVSS HYSRRFTPEI AKRPKVRDQE

GRINYYWTLL EPGDTIIFEA NGNLIAPRFA FALSRGFGSG IITSNAPMDE CDAKCQTPQG

AINSSLPFQN VHPVTIGECP KYVRSAKLRM VTGLRNIPSI QSRGLFGAIA GFIEGGWTGM

VDGWYGYHHQ NEQGSGYAAD QKSTQNAING ITNKVNSVIE KMNTQFTAVG KEFNKLERRM

ENLNKKVDDG FLDIWTYNAE LLVLLENERT LDFHDSNVKN LYEKVKSQLK NNAKEIGNGC

FEFYHKCNDE CMESVKNGTY DYPKYSEESK LNRERIDGVK LESMGVYQIL AIYSTVASSL

VLLVSLGAIS FWMCSNGSLQ CRICI

HEMAGGLUTININ [INFLUENZA A VIRUS (A/NEW YORK/483/2003(H1N1)) ACCESSION
ABD15515
                                                        SEQ ID NO: 10
KVKLLVLLCT FTATYADTIC IGYHANNSTD TVDTVLEKNV TVTHSVNLLE DSHNGKLCLL

KGIAPLQLGN CSVAGWILGN PECELLISKE SWSYIVETPN PENGTCYPGY FADYEELREQ

LSSVSSFERF EIFPKESSWP NHTVTGVSAS CSHNGKSSFY RNLLWLTGKN GLYPNLSKSY

ANNKEKEVLV LWGVHHPPNI GDQRALYHTE NAYISVVSSH YSRRFTPEIA KRPKVRDQEG

RINYYWTLLE PGDTIIFEAN GNLIAPRYAF ALSRGFGSGI ITSNAPMDEC DAKCQTPQGA

INSSLPFQNV HPVTIGECPK YVRSAKLRMV TGLRNIPSIQ SRGLFGAIAG FIEGGWTGMV

DGWYGYHHQN EQGSGYAADQ KSTQNAINGI TNKVNSVIEK MNTQFTAVGK EFNKLERRME

NLNKKVDDGF LDIWTYNAEL LVLLENERTL DFHDSNVKNL YEKVKSQLKN NAKEIGNGCF

EFYHKCNDEC MESVKNGTYD YPRYSEESKL NREKIDGVKL ESMGVYQILA IYSTVASSLV
```

```
LLVSLGAISF WMCSNGSLQC RICI

HEMAGGLUTININ [INFLUENZA A VIRUS (A/BRISBANE/10/2007(H3N2))ACCESSION
ABW23422
                                                      SEQ ID NO: 11
QKLPGNDNST ATLCLGHHAV PNGTIVKTIT NDQIEVTNAT ELVQSSSTGE ICDSPHQILD

GENCTLIDAL LGDPQCDGFQ NKKWDLFVER SKAYSNCYPY DVPDYASLRS LVASSGTLEF

NNESFNWTGV TQNGTSSACI RRSNNSFFSR LNWLTHLKFK YPALNVTMPN NEKFDKLYIW

GVHHPGTDND QIFPYAQASG RITVSTKRSQ QTVIPNIGSR PRVRNIPSRI SIYWTIVKPG

DILLINSTGN LIAPRGYFKI RSGKSSIMRS DAPIGKCNSE CITPNGSIPN DKPFQNVNRI

TYGACPRYVK QNTLKLATGM RNVPEKQTRG IFGAIAGFIE NGWEGMVDGW YGFRHQNSEG

IGQAADLKST QAAIDQINGK LNRLIGKTNE KFHQIEKEFS EVEGRIQDLE KYVEDTKIDL

WSYNAELLVA LENQHTIDLT DSEMNKLFEK TKKQLRENAE DMGNGCFKIY HKCDNACIGS

IRNGTYDHDV YRDEALNNRF QIKGVELKSG YKDWILWISF AISCFLLCVA LLGFIMWACQ

KGNIRCNI

HEMAGGLUTININ [INFLUENZA A VIRUS (A/WISCONSIN/34/2007(H3N2))ACCESSION
ACB11766
                                                      SEQ ID NO: 12
MKTIIALSYI LCLVFAQKLP GNDNSTATLC LGHHAVPNGT IVKTITNDQI EVTNATELVQ

SSSTGKICNS PHQILDGENC TLIDALLGDP QCDGFQNKKW DLFVERSKAS SNCYPYDVPD

YASLRSLVAS SGTLEFNNES FNWTGVTQNG TSSACIRRSN NSFFSRLNWL THLKFKYPAL

NVTMPNNEKF DKLYIWGVHH PGTDNDQIFL YAQATGRITV STKRSQQTVI PNIGSRPRVR

NIPSRISIYW TIVKPGDIFL INSTGNLIAP RGYFKIQSGK SSIMRSDAPI GKCNSECITP

NGSIPNDKPF QNVNRITYGA CPRYVKQNTL KLATGMRNVP EKQTRGIFGA IAGFIENGWE

GMVDGWYGFR HQNSEGIGQA ADLKSTQAAI DQINGKLNRL IGKTNEKFHQ IEKEFSEVEG

RIQDLEKYVE DTKIDLWSYN AELLVALENQ HTIDLTDSEM NKLFEKTKKQ LRENAEDMGN

GCFKIYHKCD NACIGSIRNG TYDHDVYRDE ALNNRFQIKG IELKSGYKDW ILWISFAISC

FLLCVALLGF IMWACQKGNI RCNICI

HEMAGGLUTININ [INFLUENZA A VIRUS (A/MANAGUA/2/2007(H3N2))ACCESSION
ACD85528,
                                                      SEQ ID NO: 13
MKTIIALSYI LCLVFAQKLP GNDNSTATLC LGHHAVPNGT IVKTITNDQI EVTNATELVQ

SSSTGEICDS PHQILDGENC TLIDALLGDP QCDGFQNKKW DLFVERSKAY SNCYPYDVPD

YVSLRSLVAS SGTLEFNNES FNWTGVTQNG TSSACIRRSN KSFFSRLNWL THLKFKYPAL

NVTMPNNENF DKLYIWGVHH PGTDNDQIFL YAQASGRITV STKRSQQTVI PNIGSRPRVR

NIPSRISIYW TIVKPGDILL INSTGNLIAP RGYFKIRSGK SSIMRSDAPI GKCNSECITP

NGSIPNDKPF QNVNRITYGA CPRYVKQNTL KLATGMRNVP EKQTRGIFGA IAGFIENGWE

GMVDGWYGFR HQNSEGIGQA ADLKSTQAAI DQINGKLNRL IGKTNEKFHQ IEKEFSEVEG

RIQDLEKYVE DTKIDLWSYN AELLVALENQ HTIDLTDSEM NKLFEKTKKQ LRENAEDLGN

GCFKIYHKCD NACIGSIRNG TYDHDVYRDE ALNNRFQIKG VELKSGYKDW ILWISFAISC

FLLCVALLGF IMWACQKGNI RCNICI hemagglutinin Influenza A virus HA1 subunit (A/Korea/426/68(H2N2))
(AA 3-345 out of 1-652 precursor)
                                                      SEQ ID NO: 14
DQICIGYHAN NSTEKVDTIL ERNVTVTHAK DILEKTHNGK LCKLNGIPPL ELGDCSIAGW

LLGNPECDRL LSVPEWSYIM EKENPRYSLC YPGSFNDYEE LKHLLSSVKH FEKVKILPKD

RWTQHTTTGG SWACAVSGKP SFFRNMVWLT RKGSNYPVAK GSYNNTSGEQ MLIIWGVHHP
```

-continued

NDEAEQRALY QNVGTYVSVA TSTLYKRSIP EIAARPKVNG LGRRMEFSWT LLDMWDTINF

ESTGNLVAPE YGFKISKRGS SGIMKTEGTL ENCETKCQTP LGAINTTLPF HNVHPLTIGE

CPKYVKSEKL VLATGLRNVP QIESR

Hemagglutinin Influenza A virus full length (A/egret/Egypt/1162-
NAMRU3/2006(H5N1))
SEQ ID NO: 15
QICIGYHANN STEQVDTIME KNVTVTHAQD ILEKTHNGKL CDLDGVKPLI LRDCSVAGWL

LGNPMCDEFL NVPEWSYIVE KINPANDLCY PGNFNDYEEL KHLLSRINHF EKIQIIPKSS

WSDHEASSGV SSACPYQGRS SFFRNVVWLI KKDNAYPTIK RSYNNTNQED LLVLWGIHHP

NDAAEQTRLY QNPTTYISVG TSTLNQRLVP KIATRSKVNG QSGRMEFFWT ILKSNDAINF

ESNGNFIAPE NAYKIVKKGD STIMKSELEY GNCNTKCQTP IGAINSSMPF HNIHPLTIGE

CPKYVKSNRL VLATGLRNSP QGERRRKKRG LFGAIAGFIE GGWQGMVDGW YGYHHSNEQG

SGYAADKEST QKAIDGVTNK VNSIIDKMNT QFEAVGREFN NLERRIENLN KKMEDGFLDV

WTYNAELLVL MENERTLDFH DSNVKNLYDK VRLQLRDNAK ELGNGCFEFY HRCDNECMES

VRNGTYDYPQ YSEEARLKRE EISGVKLESI GTYQILSIYS TVASSLALAI MVAGL

INFLUENZA VIRUS M2 PROTEIN FROM TYPE A VIRUS (H5N1) ACCESSION NO.
BAD89348 (AA 1-97)
SEQ ID NO: 16
MSLLTEVETP TRNEWECRCS DSSDPLVVAA SIIGILHLIL WILDRLFFKC IYRRLKYGLK

RGPSTAGVPE SMREEYRQEQ QSAVDVDDGH FVNIELE

TRUNCATED ENVELOPE GLYCOPROTEIN HUMAN IMMUNODEFICIENCY VIRUS 2
ACCESSION ABC39624
SEQ ID NO: 17
AFLLTSACLI YCKQYVTVFY GIPAWKNASI PLFCATRNRD TWGTIQCLPD

NDDYQEIVLN VAEAFDAWDN TVTEQAIEDV WNLFETSTKP CVKLTPLCVT MRCNTSTTTT

TTAPTSTSAG STATPKPIMV NENTSCMHAN NCSGLGEEEV VNCEFNMTGL VRDKPKTYNE

TWYSRDVDCE PDSTTNSRKC YMNHCNTSVI TESCDKHYWD DIRFRYCAPP GYALLRCNDT

NYSGFAPNCS KVVASTCTRM METQTSTWFG FNGTRAENRT YLYWHSKSDR TIISLNKYYN

LSIHCKRPGN KTVTPITLMS GYKFHSRPVI NTRPKQAWCW FKGRWKDAMQ EVKKTVAEHP

RAVTKDPKNI TFAAPGKGSD PEVEYMWTNC RGEFLYCDMT WFLDWIENRP TRKAWRNYVP

CHIRQIINTW HKVGKHVYLP PREGELTCNS TVTSIIANID VNEIDKRTNI TFSAEVAELY

RVELGDYKLV EVTPIGFAPT SEKRYSSGHR ETYKRCARAR ILGFSRNSRF CNGRSVLDAV

RSAPDFTGRD SAATATAVGR GQETTRNVAT DRLGNEKSPG KSHCYREIPK GSGAAKFMGM

CV

GP120 HUMAN IMMUNODEFICIENCY VIRUS TYPE 1 ACCESSION AAF69492
SEQ ID NO: 18
VPVWRDADTT LFCASDAKSH VTEAHNVWAT HACVPTDPNP QEIHLENVTE NFNMWKNNMV

EQMQEDVISL WEQSLKPCVK LTPLCVTLNC TNANLTNANL TNANNITNVE NITDEVRNCS

FNVTTDLRDK QQKVHALFYR LDIVQINSKN SSDYRLINCN TSVIKQACPK ISFDPIPIHY

CTPAGYAILK CNDKNFNGTG PCKNVSSVQC THGIKPVVST QLLLNGSLAE EEIIIRSENL

TNNVKTIIVH LNKSVEINCT RPSNNTRTSI TIGPGQVFYR TGDIIGDIRK VSCELNGTKW

NEVLKQVKEK LKEHFNKNIS FQPPSGGDLE ITMHHFSCRG EFFYCNTTQL FNNTYSNGTI

TLPCKIKQII NMWQGVGQAM YAPPISGRIN CLSNITGLLL TRDGNNGTNE TFRPGGGNIK

DNWRSELYKC KVVQIEPLGI APTRAKRRVV EREKK

ENVELOPE GLYCOPROTEIN I HUMAN HERPESVIRUS 3 ACCESSION NP_040189

-continued

SEQ ID NO: 19

MFLIQCLISA VIFYIQVTNA LIFKGDHVSL QVNSSLTSIL IPMQNDNYTE IKGQLVFIGE

QLPTGTNYSG TLELLYADTV AFCFRSVQVI RYDGCPRIRT SAFISCRYKH SWHYGNSTDR

ISTEPDAGVM LKITKPGIND AGVYVLLVRL DHSRSTDGFI LGVNVYTAGS HHNIHGVIYT

SPSLQNGYST RALFQQARLC DLPATPKGSG TSLFQHMLDL RAGKSLEDNP WLHEDVVTTE

TKSVVKEGIE NHVYPTDMST LPEKSLNDPP ENLLIIIPIV ASVMILTAMV IVIVISVKRR

RIKKHPIYRP NTKTRRGIQN ATPESDVMLE AAIAQLATIR EESPPHSVVN PFVK

The claims of the invention are:

1. A process for manufacturing a composition comprising directed-sequence polymers (DSPs) useful for eliciting immune responses in a subject, wherein the DSP composition has a complexity of greater than $5 \times 10^2$ different DSPs, comprising the steps of:
    (a) selecting a first base peptide sequence, wherein the base peptide sequence comprises an amino acid sequence of an epitope of an antigen associated with a disease, which disease is an infectious disease, and wherein the length of the sequence is at least 6 amino acids;
    (b) synthesizing by solid-phase peptide synthesis a first cassette of the DSPs, the cassette having a sequence of amino acid positions corresponding to each amino acid of the first base peptide sequence,
        wherein, for at least one amino acid position of the first cassette, an amino acid is added, the amino acid for each said position being randomly selected from a mixture of two or more amino acids consisting of the original amino acid found at that amino acid position, optionally alanine (A), and, optionally, at least one conserved substitution
        wherein the amino acids in the mixture are present in a fixed molar input ratio relative to each other, determined prior to starting synthesis,
        wherein the relative molar amount of A is more than 10% and less than 90% of the total amino acid concentration of the DSPs;
    (c) optionally further extending the length of the DSPs by selecting a step from the group consisting of:
        (i) repeating step (b) for 2 to 15 cycles and elongating the DSP under the same condition including the input ratio of amino acids in the mixture;
        (ii) repeating step (b) for 2 to 15 cycles and elongating the DSP, for each cycle, using a different input ratio of amino acids in the mixture;
        (iii) repeating steps (a) and (b) for 2 to 15 cycles and elongating the DSP using cassettes based on more than one base peptide;
        (iv) assembling 2 to 15 cassettes synthesized in a single cycle of step (b); and
        (v) assembling 2 to 15 cassettes, the first cassette synthesized under one condition of step (b), and second and more cassettes synthesized under one or more different conditions of step (b);
    wherein the number of cycles selected in step (c) is selected so that the final length of the DSP is about 25 to 300 amino acid residues.

2. The process according to claim 1, wherein the first base peptide sequence comprises a known epitope sequence which is a partial sequence of SEQ ID NO: 1 through 19.

3. The process according to claim 1, wherein the infectious disease is a viral infection.

4. The process according to claim 3, wherein the viral infection is caused by an influenza virus.

5. The process according to claim 1, wherein the infectious disease is a parasitic infection.

6. The process according to claim 3, wherein the infectious disease is selected from AIDS, AIDS Related Complex, Chickenpox (Varicella), Common cold, Cytomegalovirus Infection, Colorado tick fever, Dengue fever, Ebola haemorrhagic fever, Hand, foot and mouth disease, Hepatitis, Herpes simplex, Herpes zoster, HPV, Influenza (Flu), Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever.

7. The process according to claim 1, wherein the final average length of DSPs is between about 30 amino acids to 150 amino acids.

8. The process according to claim 1, wherein the relative molar concentration of alanine in the final DSP composition is between about 15% and 70%.

9. The process according to claim 1, wherein the relative molar concentration of alanine in the final DSP composition is between about 20% and 50%.

10. The process of claim 1, wherein the DSPs in the composition have more than one cassette.

11. The process of claim 1, wherein the DSP composition has a complexity of greater than $1\times10^6$ different DSPs based on the first base peptide sequence.

12. The process of claim 1, wherein the conserved substitution is selected from amino acids found as naturally occurring variations in accordance with differences at a given position between species or within variants of the same species of organism the epitope is derived from.

13. The process according to claim 1, wherein the infectious disease is a bacterial infection.

14. The process according to claim 1, which further comprises introducing a disulfide bond into one or more DSPs.

15. The process according to claim 1, which further comprises introducing glycosylation into one or more DSPs.

16. The process according to claim 1, wherein, for at least one amino acid position of the first cassette, an amino acid is sequentially incorporated into the DSP, such amino acid for each said position randomly selected from a mixture of amino acids consisting of the original amino acid found at that amino acid position, alanine (A), and, optionally, at least one conserved substitution.

17. The process according to claim 1, wherein the relative molar concentration of alanine in the final DSP composition is between about 15% and 35%.

* * * * *

SEQUENCE LISTING

<160> NUMBER OF SEQ ID NOS: 26

<210> SEQ ID NO 1
<211> LENGTH: 10
<212> TYPE: PRT
<213> ORGANISM: Human cytomegalovirus

<400> SEQUENCE: 1

Ile Leu Ala Arg Asn Leu Val Pro Met Val
1               5                   10

<210> SEQ ID NO 2
<211> LENGTH: 9
<212> TYPE: PRT
<213> ORGANISM: Human cytomegalovirus

<400> SEQUENCE: 2

Glu Leu Glu Gly Val Trp Gln Pro Ala
1               5

<210> SEQ ID NO 3
<211> LENGTH: 9
<212> TYPE: PRT
<213> ORGANISM: Human cytomegalovirus

<400> SEQUENCE: 3

Arg Ile Phe Ala Glu Leu Glu Gly Val
1               5

<210> SEQ ID NO 4
<211> LENGTH: 9
<212> TYPE: PRT
<213> ORGANISM: Human cytomegalovirus

<400> SEQUENCE: 4

Asn Leu Val Pro Met Val Ala Thr Val
1               5

<210> SEQ ID NO 5
<211> LENGTH: 15
<212> TYPE: PRT
<213> ORGANISM: Human immunodeficiency virus

<400> SEQUENCE: 5

Arg Ile Gln Arg Gly Pro Gly Arg Ala Phe Val Thr Ile Gly Lys
1               5                   10                  15

<210> SEQ ID NO 6
<211> LENGTH: 126
<212> TYPE: PRT
<213> ORGANISM: Influenza A virus

<400> SEQUENCE: 6

Ile Ile Pro Lys Ser Ser Trp Ser Asp His Glu Ala Ser Ser Gly Val
1               5                   10                  15

Ser Ser Ala Cys Pro Tyr Gln Gly Arg Ser Ser Phe Phe Arg Asn Val
            20                  25                  30

Val Trp Leu Ile Lys Lys Asp Asn Ala Tyr Pro Thr Ile Lys Arg Ser
        35                  40                  45

Tyr Asn Asn Thr Asn Gln Glu Asp Leu Leu Val Leu Trp Gly Ile His
    50                  55                  60

His Pro Asn Asp Ala Ala Glu Gln Thr Arg Leu Tyr Gln Asn Pro Thr
65                  70                  75                  80

Thr Tyr Ile Ser Val Gly Thr Ser Thr Leu Asn Gln Arg Leu Val Pro
                85                  90                  95

Lys Ile Ala Thr Arg Ser Lys Val Asn Gly Gln Ser Gly Arg Met Glu
            100                 105                 110

Phe Phe Trp Thr Ile Leu Lys Ser Asn Asp Ala Ile Asn Phe
            115                 120                 125

<210> SEQ ID NO 7
<211> LENGTH: 51
<212> TYPE: PRT
<213> ORGANISM: Influenza A virus

<400> SEQUENCE: 7

Cys Ile Ile Pro Lys Ser Ser Trp Ser Asp His Glu Ala Ser Ser Gly
1               5                   10                  15

Val Ser Ser Ala Cys Pro Tyr Gln Gly Arg Ser Ser Phe Phe Arg Asn
            20                  25                  30

Val Val Trp Leu Ile Lys Lys Asp Asn Ala Tyr Pro Thr Ile Lys Arg
        35                  40                  45

Ser Tyr Cys
    50

<210> SEQ ID NO 8
<211> LENGTH: 565
<212> TYPE: PRT
<213> ORGANISM: Influenza A virus

<400> SEQUENCE: 8

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr

```
            130                 135                 140
Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
                180                 185                 190

Trp Gly Val His His Pro Pro Asn Ile Gly Asp Gln Lys Ala Leu Tyr
            195                 200                 205

His Thr Glu Asn Ala Tyr Val Ser Val Val Ser Ser His Tyr Ser Arg
        210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
                260                 265                 270

Leu Ser Arg Gly Phe Gly Ser Gly Ile Ile Asn Ser Asn Ala Pro Met
            275                 280                 285

Asp Lys Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560
```

```
Cys Arg Ile Cys Ile
                565

<210> SEQ ID NO 9
<211> LENGTH: 565
<212> TYPE: PRT
<213> ORGANISM: Influenza A virus

<400> SEQUENCE: 9

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Gly Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asx Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Phe Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
```

```
                355                 360                 365
His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Arg Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 10
<211> LENGTH: 564
<212> TYPE: PRT
<213> ORGANISM: Influenza A virus

<400> SEQUENCE: 10

Lys Val Lys Leu Leu Val Leu Leu Cys Thr Phe Thr Ala Thr Tyr Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Ser His Asn Gly Lys Leu Cys Leu Leu Lys Gly Ile Ala
    50                  55                  60

Pro Leu Gln Leu Gly Asn Cys Ser Val Ala Gly Trp Ile Leu Gly Asn
65                  70                  75                  80

Pro Glu Cys Glu Leu Leu Ile Ser Lys Glu Ser Trp Ser Tyr Ile Val
                85                  90                  95

Glu Thr Pro Asn Pro Glu Asn Gly Thr Cys Tyr Pro Gly Tyr Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Ser Ser Trp Pro Asn His Thr Val
    130                 135                 140

Thr Gly Val Ser Ala Ser Cys Ser His Asn Gly Lys Ser Ser Phe Tyr
145                 150                 155                 160
```

Arg Asn Leu Leu Trp Leu Thr Gly Lys Asn Gly Leu Tyr Pro Asn Leu
                165                 170                 175

Ser Lys Ser Tyr Ala Asn Asn Lys Glu Lys Glu Val Leu Val Leu Trp
            180                 185                 190

Gly Val His His Pro Pro Asn Ile Gly Asp Gln Arg Ala Leu Tyr His
            195                 200                 205

Thr Glu Asn Ala Tyr Ile Ser Val Val Ser Ser His Tyr Ser Arg Arg
210                 215                 220

Phe Thr Pro Glu Ile Ala Lys Arg Pro Lys Val Arg Asp Gln Glu Gly
225                 230                 235                 240

Arg Ile Asn Tyr Tyr Trp Thr Leu Leu Glu Pro Gly Asp Thr Ile Ile
                245                 250                 255

Phe Glu Ala Asn Gly Asn Leu Ile Ala Pro Arg Tyr Ala Phe Ala Leu
                260                 265                 270

Ser Arg Gly Phe Gly Ser Gly Ile Ile Thr Ser Asn Ala Pro Met Asp
            275                 280                 285

Glu Cys Asp Ala Lys Cys Gln Thr Pro Gln Gly Ala Ile Asn Ser Ser
290                 295                 300

Leu Pro Phe Gln Asn Val His Pro Val Thr Ile Gly Glu Cys Pro Lys
305                 310                 315                 320

Tyr Val Arg Ser Ala Lys Leu Arg Met Val Thr Gly Leu Arg Asn Ile
                325                 330                 335

Pro Ser Ile Gln Ser Arg Gly Leu Phe Gly Ala Ile Ala Gly Phe Ile
                340                 345                 350

Glu Gly Gly Trp Thr Gly Met Val Asp Gly Trp Tyr Gly Tyr His His
            355                 360                 365

Gln Asn Glu Gln Gly Ser Gly Tyr Ala Ala Asp Gln Lys Ser Thr Gln
370                 375                 380

Asn Ala Ile Asn Gly Ile Thr Asn Lys Val Asn Ser Val Ile Glu Lys
385                 390                 395                 400

Met Asn Thr Gln Phe Thr Ala Val Gly Lys Glu Phe Asn Lys Leu Glu
                405                 410                 415

Arg Arg Met Glu Asn Leu Asn Lys Lys Val Asp Asp Gly Phe Leu Asp
                420                 425                 430

Ile Trp Thr Tyr Asn Ala Glu Leu Leu Val Leu Leu Glu Asn Glu Arg
            435                 440                 445

Thr Leu Asp Phe His Asp Ser Asn Val Lys Asn Leu Tyr Glu Lys Val
450                 455                 460

Lys Ser Gln Leu Lys Asn Asn Ala Lys Glu Ile Gly Asn Gly Cys Phe
465                 470                 475                 480

Glu Phe Tyr His Lys Cys Asn Asp Glu Cys Met Glu Ser Val Lys Asn
                485                 490                 495

Gly Thr Tyr Asp Tyr Pro Arg Tyr Ser Glu Glu Ser Lys Leu Asn Arg
            500                 505                 510

Glu Lys Ile Asp Gly Val Lys Leu Glu Ser Met Gly Val Tyr Gln Ile
            515                 520                 525

Leu Ala Ile Tyr Ser Thr Val Ala Ser Ser Leu Val Leu Leu Val Ser
530                 535                 540

Leu Gly Ala Ile Ser Phe Trp Met Cys Ser Asn Gly Ser Leu Gln Cys
545                 550                 555                 560

Arg Ile Cys Ile

<210> SEQ ID NO 11

<211> LENGTH: 548
<212> TYPE: PRT
<213> ORGANISM: Influenza A virus

<400> SEQUENCE: 11

```
Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gl

```
            385                 390                 395                 400
            Glu Val Glu Gly Arg Ile Gln Asp Leu Glu Lys Tyr Val Glu Asp Thr
                            405                 410                 415

Lys Ile Asp Leu Trp Ser Tyr Asn Ala Glu Leu Leu Val Ala Leu Glu
                            420                 425                 430

Asn Gln His Thr Ile Asp Leu Thr Asp Ser Glu Met Asn Lys Leu Phe
                            435                 440                 445

Glu Lys Thr Lys Lys Gln Leu Arg Glu Asn Ala Glu Asp Met Gly Asn
                            450                 455                 460

Gly Cys Phe Lys Ile Tyr His Lys Cys Asp Asn Ala Cys Ile Gly Ser
            465                 470                 475                 480

Ile Arg Asn Gly Thr Tyr Asp His Asp Val Tyr Arg Asp Glu Ala Leu
                            485                 490                 495

Asn Asn Arg Phe Gln Ile Lys Gly Val Glu Leu Lys Ser Gly Tyr Lys
                            500                 505                 510

Asp Trp Ile Leu Trp Ile Ser Phe Ala Ile Ser Cys Phe Leu Leu Cys
                            515                 520                 525

Val Ala Leu Leu Gly Phe Ile Met Trp Ala Cys Gln Lys Gly Asn Ile
                            530                 535                 540

Arg Cys Asn Ile
            545

<210> SEQ ID NO 12
<211> LENGTH: 566
<212> TYPE: PRT
<213> ORGANISM: Influenza A virus

<400> SEQUENCE: 12

Met Lys Thr Ile Ile Ala Leu Ser Tyr Ile Leu Cys Leu Val Phe Ala
            1               5                   10                  15

Gln Lys Leu Pro Gly Asn Asp Asn Ser Thr Ala Thr Leu Cys Leu Gly
                            20                  25                  30

His His Ala Val Pro Asn Gly Thr Ile Val Lys Thr Ile Thr Asn Asp
                            35                  40                  45

Gln Ile Glu Val Thr Asn Ala Thr Glu Leu Val Gln Ser Ser Ser Thr
                50                  55                  60

Gly Lys Ile Cys Asn Ser Pro His Gln Ile Leu Asp Gly Glu Asn Cys
            65                  70                  75                  80

Thr Leu Ile Asp Ala Leu Leu Gly Asp Pro Gln Cys Asp Gly Phe Gln
                            85                  90                  95

Asn Lys Lys Trp Asp Leu Phe Val Glu Arg Ser Lys Ala Ser Ser Asn
                            100                 105                 110

Cys Tyr Pro Tyr Asp Val Pro Asp Tyr Ala Ser Leu Arg Ser Leu Val
                            115                 120                 125

Ala Ser Ser Gly Thr Leu Glu Phe Asn Asn Glu Ser Phe Asn Trp Thr
                130                 135                 140

Gly Val Thr Gln Asn Gly Thr Ser Ser Ala Cys Ile Arg Arg Ser Asn
            145                 150                 155                 160

Asn Ser Phe Phe Ser Arg Leu Asn Trp Leu Thr His Leu Lys Phe Lys
                            165                 170                 175

Tyr Pro Ala Leu Asn Val Thr Met Pro Asn Asn Glu Lys Phe Asp Lys
                            180                 185                 190

Leu Tyr Ile Trp Gly Val His His Pro Gly Thr Asp Asn Asp Gln Ile
                            195                 200                 205
```

Phe Leu Tyr Ala Gln Ala Thr Gly Arg Ile Thr Val Ser Thr Lys Arg
            210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Phe Leu Ile Asn Ser Thr Gly Asn Leu Ile Ala Pro Arg Gly
            260                 265                 270

Tyr Phe Lys Ile Gln Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Ile Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 13
<211> LENGTH: 566
<212> TYPE: PRT
<213> ORGANISM: Influenza A virus

<400> SEQUENCE: 13

Met Lys Thr Ile Ile Ala Leu Ser Tyr Ile Leu Cys Leu Val Phe Ala
1               5                   10                  15

-continued

```
Gln Lys Leu Pro Gly Asn Asp Asn Ser Thr Ala Thr Leu Cys Leu Gly
             20                  25                  30

His His Ala Val Pro Asn Gly Thr Ile Val Lys Thr Ile Thr Asn Asp
         35                  40                  45

Gln Ile Glu Val Thr Asn Ala Thr Glu Leu Val Gln Ser Ser Ser Thr
 50                  55                  60

Gly Glu Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Val Ser Leu Arg Ser Leu Val
            115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Lys Ser Phe Phe Ser Arg Leu Asn Trp Leu Thr His Leu Lys Phe Lys
                165                 170                 175

Tyr Pro Ala Leu Asn Val Thr Met Pro Asn Asn Glu Asn Phe Asp Lys
            180                 185                 190

Leu Tyr Ile Trp Gly Val His His Pro Gly Thr Asp Asn Asp Gln Ile
            195                 200                 205

Phe Leu Tyr Ala Gln Ala Ser Gly Arg Ile Thr Val Ser Thr Lys Arg
            210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
            290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Ile Gly Gln Ala Ala Asp Leu Lys
            370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430
```

```
Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Leu Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 14
<211> LENGTH: 325
<212> TYPE: PRT
<213> ORGANISM: Influenza A virus

<400> SEQUENCE: 14

Asp Gln Ile Cys Ile Gly Tyr His Ala Asn Asn Ser Thr Glu Lys Val
1               5                   10                  15

Asp Thr Ile Leu Glu Arg Asn Val Thr Val Thr His Ala Lys Asp Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Ser Val Pro Glu Trp Ser Tyr Ile Met
65                  70                  75                  80

Glu Lys Glu Asn Pro Arg Tyr Ser Leu Cys Tyr Pro Gly Ser Phe Asn
                85                  90                  95

Asp Tyr Glu Glu Leu Lys His Leu Leu Ser Ser Val Lys His Phe Glu
            100                 105                 110

Lys Val Lys Ile Leu Pro Lys Asp Arg Trp Thr Gln His Thr Thr Thr
        115                 120                 125

Gly Gly Ser Trp Ala Cys Ala Val Ser Gly Lys Pro Ser Phe Phe Arg
    130                 135                 140

Asn Met Val Trp Leu Thr Arg Lys Gly Ser Asn Tyr Pro Val Ala Lys
145                 150                 155                 160

Gly Ser Tyr Asn Asn Thr Ser Gly Glu Gln Met Leu Ile Ile Trp Gly
                165                 170                 175

Val His His Pro Asn Asp Glu Ala Glu Gln Arg Ala Leu Tyr Gln Asn
            180                 185                 190

Val Gly Thr Tyr Val Ser Val Ala Thr Ser Thr Leu Tyr Lys Arg Ser
        195                 200                 205

Ile Pro Glu Ile Ala Ala Arg Pro Lys Val Asn Gly Leu Gly Arg Arg
    210                 215                 220

Met Glu Phe Ser Trp Thr Leu Leu Asp Met Trp Asp Thr Ile Asn Phe
225                 230                 235                 240
```

```
Glu Ser Thr Gly Asn Leu Val Ala Pro Glu Tyr Gly Phe Lys Ile Ser
                245                 250                 255

Lys Arg Gly Ser Ser Gly Ile Met Lys Thr Glu Gly Thr Leu Glu Asn
            260                 265                 270

Cys Glu Thr Lys Cys Gln Thr Pro Leu Gly Ala Ile Asn Thr Thr Leu
        275                 280                 285

Pro Phe His Asn Val His Pro Leu Thr Ile Gly Glu Cys Pro Lys Tyr
    290                 295                 300

Val Lys Ser Glu Lys Leu Val Leu Ala Thr Gly Leu Arg Asn Val Pro
305                 310                 315                 320

Gln Ile Glu Ser Arg
                325

<210> SEQ ID NO 15
<211> LENGTH: 535
<212> TYPE: PRT
<213> ORGANISM: Influenza A virus

<400> SEQUENCE: 15

Gln Ile Cys Ile Gly Tyr His Ala Asn Asn Ser Thr Glu Gln Val Asp
1               5                   10                  15

Thr Ile Met Glu Lys Asn Val Thr Val Thr His Ala Gln Asp Ile Leu
            20                  25                  30

Glu Lys Thr His Asn Gly Lys Leu Cys Asp Leu Asp Gly Val Lys Pro
        35                  40                  45

Leu Ile Leu Arg Asp Cys Ser Val Ala Gly Trp Leu Leu Gly Asn Pro
    50                  55                  60

Met Cys Asp Glu Phe Leu Asn Val Pro Glu Trp Ser Tyr Ile Val Glu
65                  70                  75                  80

Lys Ile Asn Pro Ala Asn Asp Leu Cys Tyr Pro Gly Asn Phe Asn Asp
                85                  90                  95

Tyr Glu Glu Leu Lys His Leu Leu Ser Arg Ile Asn His Phe Glu Lys
            100                 105                 110

Ile Gln Ile Ile Pro Lys Ser Ser Trp Ser Asp His Glu Ala Ser Ser
        115                 120                 125

Gly Val Ser Ser Ala Cys Pro Tyr Gln Gly Arg Ser Ser Phe Phe Arg
    130                 135                 140

Asn Val Val Trp Leu Ile Lys Lys Asp Asn Ala Tyr Pro Thr Ile Lys
145                 150                 155                 160

Arg Ser Tyr Asn Asn Thr Asn Gln Glu Asp Leu Leu Val Leu Trp Gly
                165                 170                 175

Ile His His Pro Asn Asp Ala Ala Glu Gln Thr Arg Leu Tyr Gln Asn
            180                 185                 190

Pro Thr Thr Tyr Ile Ser Val Gly Thr Ser Thr Leu Asn Gln Arg Leu
        195                 200                 205

Val Pro Lys Ile Ala Thr Arg Ser Lys Val Asn Gly Gln Ser Gly Arg
    210                 215                 220

Met Glu Phe Phe Trp Thr Ile Leu Lys Ser Asn Asp Ala Ile Asn Phe
225                 230                 235                 240

Glu Ser Asn Gly Asn Phe Ile Ala Pro Glu Asn Ala Tyr Lys Ile Val
                245                 250                 255

Lys Lys Gly Asp Ser Thr Ile Met Lys Ser Glu Leu Glu Tyr Gly Asn
            260                 265                 270

Cys Asn Thr Lys Cys Gln Thr Pro Ile Gly Ala Ile Asn Ser Ser Met
```

```
                275                 280                 285
Pro Phe His Asn Ile His Pro Leu Thr Ile Gly Glu Cys Pro Lys Tyr
290                 295                 300
Val Lys Ser Asn Arg Leu Val Leu Ala Thr Gly Leu Arg Asn Ser Pro
305                 310                 315                 320
Gln Gly Glu Arg Arg Lys Lys Arg Gly Leu Phe Gly Ala Ile Ala
            325                 330                 335
Gly Phe Ile Glu Gly Gly Trp Gln Gly Met Val Asp Gly Trp Tyr Gly
                340                 345                 350
Tyr His His Ser Asn Glu Gln Gly Ser Gly Tyr Ala Ala Asp Lys Glu
            355                 360                 365
Ser Thr Gln Lys Ala Ile Asp Gly Val Thr Asn Lys Val Asn Ser Ile
370                 375                 380
Ile Asp Lys Met Asn Thr Gln Phe Glu Ala Val Gly Arg Glu Phe Asn
385                 390                 395                 400
Asn Leu Glu Arg Arg Ile Glu Asn Leu Asn Lys Lys Met Glu Asp Gly
            405                 410                 415
Phe Leu Asp Val Trp Thr Tyr Asn Ala Glu Leu Leu Val Leu Met Glu
                420                 425                 430
Asn Glu Arg Thr Leu Asp Phe His Asp Ser Asn Val Lys Asn Leu Tyr
            435                 440                 445
Asp Lys Val Arg Leu Gln Leu Arg Asp Asn Ala Lys Glu Leu Gly Asn
450                 455                 460
Gly Cys Phe Glu Phe Tyr His Arg Cys Asp Asn Glu Cys Met Glu Ser
465                 470                 475                 480
Val Arg Asn Gly Thr Tyr Asp Tyr Pro Gln Tyr Ser Glu Glu Ala Arg
            485                 490                 495
Leu Lys Arg Glu Glu Ile Ser Gly Val Lys Leu Glu Ser Ile Gly Thr
                500                 505                 510
Tyr Gln Ile Leu Ser Ile Tyr Ser Thr Val Ala Ser Ser Leu Ala Leu
            515                 520                 525
Ala Ile Met Val Ala Gly Leu
530                 535

<210> SEQ ID NO 16
<211> LENGTH: 97
<212> TYPE: PRT
<213> ORGANISM: Influenza A virus

<400> SEQUENCE: 16

Met Ser Leu Leu Thr Glu Val Glu Thr Pro Thr Arg Asn Glu Trp Glu
1               5                   10                  15
Cys Arg Cys Ser Asp Ser Ser Asp Pro Leu Val Val Ala Ala Ser Ile
            20                  25                  30
Ile Gly Ile Leu His Leu Ile Leu Trp Ile Leu Asp Arg Leu Phe Phe
        35                  40                  45
Lys Cys Ile Tyr Arg Arg Leu Lys Tyr Gly Leu Lys Arg Gly Pro Ser
    50                  55                  60
Thr Ala Gly Val Pro Glu Ser Met Arg Glu Glu Tyr Arg Gln Glu Gln
65                  70                  75                  80
Gln Ser Ala Val Asp Val Asp Asp Gly His Phe Val Asn Ile Glu Leu
            85                  90                  95
Glu
```

```
<210> SEQ ID NO 17
<211> LENGTH: 592
<212> TYPE: PRT
<213> ORGANISM: Human immunodeficiency virus

<400> SEQUENCE: 17

Ala Phe Leu Leu Thr Ser Ala Cys Leu Ile Tyr Cys Lys Gln Tyr Val
 1               5                  10                  15

Thr Val Phe Tyr Gly Ile Pro Ala Trp Lys Asn Ala Ser Ile Pro Leu
            20                  25                  30

Phe Cys Ala Thr Arg Asn Arg Asp Thr Trp Gly Thr Ile Gln Cys Leu
        35                  40                  45

Pro Asp Asn Asp Asp Tyr Gln Glu Ile Val Leu Asn Val Ala Glu Ala
    50                  55                  60

Phe Asp Ala Trp Asp Asn Thr Val Thr Glu Gln Ala Ile Glu Asp Val
65                  70                  75                  80

Trp Asn Leu Phe Glu Thr Ser Thr Lys Pro Cys Val Lys Leu Thr Pro
                85                  90                  95

Leu Cys Val Thr Met Arg Cys Asn Thr Ser Thr Thr Thr Thr Thr Thr
            100                 105                 110

Ala Pro Thr Ser Thr Ser Ala Gly Ser Thr Ala Thr Pro Lys Pro Ile
        115                 120                 125

Met Val Asn Glu Asn Thr Ser Cys Met His Ala Asn Asn Cys Ser Gly
    130                 135                 140

Leu Gly Glu Glu Glu Val Val Asn Cys Glu Phe Asn Met Thr Gly Leu
145                 150                 155                 160

Val Arg Asp Lys Pro Lys Thr Tyr Asn Glu Thr Trp Tyr Ser Arg Asp
                165                 170                 175

Val Asp Cys Glu Pro Asp Ser Thr Thr Asn Ser Arg Lys Cys Tyr Met
            180                 185                 190

Asn His Cys Asn Thr Ser Val Ile Thr Glu Ser Cys Asp Lys His Tyr
        195                 200                 205

Trp Asp Asp Ile Arg Phe Arg Tyr Cys Ala Pro Pro Gly Tyr Ala Leu
    210                 215                 220

Leu Arg Cys Asn Asp Thr Asn Tyr Ser Gly Phe Ala Pro Asn Cys Ser
225                 230                 235                 240

Lys Val Val Ala Ser Thr Cys Thr Arg Met Met Glu Thr Gln Thr Ser
                245                 250                 255

Thr Trp Phe Gly Phe Asn Gly Thr Arg Ala Glu Asn Arg Thr Tyr Leu
            260                 265                 270

Tyr Trp His Ser Lys Ser Asp Arg Thr Ile Ile Ser Leu Asn Lys Tyr
        275                 280                 285

Tyr Asn Leu Ser Ile His Cys Lys Arg Pro Gly Asn Lys Thr Val Thr
    290                 295                 300

Pro Ile Thr Leu Met Ser Gly Tyr Lys Phe His Ser Arg Pro Val Ile
305                 310                 315                 320

Asn Thr Arg Pro Lys Gln Ala Trp Cys Trp Phe Lys Gly Arg Trp Lys
                325                 330                 335

Asp Ala Met Gln Glu Val Lys Lys Thr Val Ala Glu His Pro Arg Ala
            340                 345                 350

Val Thr Lys Asp Pro Lys Asn Ile Thr Phe Ala Ala Pro Gly Lys Gly
        355                 360                 365

Ser Asp Pro Glu Val Glu Tyr Met Trp Thr Asn Cys Arg Gly Glu Phe
    370                 375                 380
```

```
Leu Tyr Cys Asp Met Thr Trp Phe Leu Asp Trp Ile Glu Asn Arg Pro
385                 390                 395                 400

Thr Arg Lys Ala Trp Arg Asn Tyr Val Pro Cys His Ile Arg Gln Ile
            405                 410                 415

Ile Asn Thr Trp His Lys Val Gly Lys His Val Tyr Leu Pro Pro Arg
        420                 425                 430

Glu Gly Glu Leu Thr Cys Asn Ser Thr Val Thr Ser Ile Ile Ala Asn
            435                 440                 445

Ile Asp Val Asn Glu Ile Asp Lys Arg Thr Asn Ile Thr Phe Ser Ala
450                 455                 460

Glu Val Ala Glu Leu Tyr Arg Val Glu Leu Gly Asp Tyr Lys Leu Val
465                 470                 475                 480

Glu Val Thr Pro Ile Gly Phe Ala Pro Thr Ser Glu Lys Arg Tyr Ser
            485                 490                 495

Ser Gly His Arg Glu Thr Tyr Lys Arg Cys Ala Arg Ala Arg Ile Leu
            500                 505                 510

Gly Phe Ser Arg Asn Ser Arg Phe Cys Asn Gly Arg Ser Val Leu Asp
        515                 520                 525

Ala Val Arg Ser Ala Pro Asp Phe Thr Gly Arg Asp Ser Ala Ala Thr
530                 535                 540

Ala Thr Ala Val Gly Arg Gly Gln Glu Thr Thr Arg Asn Val Ala Thr
545                 550                 555                 560

Asp Arg Leu Gly Asn Glu Lys Ser Pro Gly Lys Ser His Cys Tyr Arg
            565                 570                 575

Glu Ile Pro Lys Gly Ser Gly Ala Ala Lys Phe Met Gly Met Cys Val
        580                 585                 590

<210> SEQ ID NO 18
<211> LENGTH: 455
<212> TYPE: PRT
<213> ORGANISM: Human immunodeficiency virus

<400> SEQUENCE: 18

Val Pro Val Trp Arg Asp Ala Asp Thr Thr Leu Phe Cys Ala Ser Asp
1               5                   10                  15

Ala Lys Ser His Val Thr Glu Ala His Asn Val Trp Ala Thr His Ala
            20                  25                  30

Cys Val Pro Thr Asp Pro Asn Pro Gln Glu Ile His Leu Glu Asn Val
        35                  40                  45

Thr Glu Asn Phe Asn Met Trp Lys Asn Asn Met Val Glu Gln Met Gln
    50                  55                  60

Glu Asp Val Ile Ser Leu Trp Glu Gln Ser Leu Lys Pro Cys Val Lys
65                  70                  75                  80

Leu Thr Pro Leu Cys Val Thr Leu Asn Cys Thr Asn Ala Asn Leu Thr
                85                  90                  95

Asn Ala Asn Leu Thr Ala Asn Asn Ile Thr Asn Val Glu Asn Ile
            100                 105                 110

Thr Asp Glu Val Arg Asn Cys Ser Phe Asn Val Thr Thr Asp Leu Arg
        115                 120                 125

Asp Lys Gln Gln Lys Val His Ala Leu Phe Tyr Arg Leu Asp Ile Val
    130                 135                 140

Gln Ile Asn Ser Lys Asn Ser Ser Asp Tyr Arg Leu Ile Asn Cys Asn
145                 150                 155                 160

Thr Ser Val Ile Lys Gln Ala Cys Pro Lys Ile Ser Phe Asp Pro Ile
                165                 170                 175
```

```
Pro Ile His Tyr Cys Thr Pro Ala Gly Tyr Ala Ile Leu Lys Cys Asn
            180                 185                 190

Asp Lys Asn Phe Asn Gly Thr Gly Pro Cys Lys Asn Val Ser Ser Val
                195                 200                 205

Gln Cys Thr His Gly Ile Lys Pro Val Val Ser Thr Gln Leu Leu Leu
    210                 215                 220

Asn Gly Ser Leu Ala Glu Glu Ile Ile Arg Ser Glu Asn Leu
225                 230                 235                 240

Thr Asn Asn Val Lys Thr Ile Ile Val His Leu Asn Lys Ser Val Glu
                245                 250                 255

Ile Asn Cys Thr Arg Pro Ser Asn Asn Thr Arg Thr Ser Ile Thr Ile
                260                 265                 270

Gly Pro Gly Gln Val Phe Tyr Arg Thr Gly Asp Ile Ile Gly Asp Ile
            275                 280                 285

Arg Lys Val Ser Cys Glu Leu Asn Gly Thr Lys Trp Asn Glu Val Leu
    290                 295                 300

Lys Gln Val Lys Glu Lys Leu Lys Glu His Phe Asn Lys Asn Ile Ser
305                 310                 315                 320

Phe Gln Pro Pro Ser Gly Gly Asp Leu Glu Ile Thr Met His His Phe
                325                 330                 335

Ser Cys Arg Gly Glu Phe Phe Tyr Cys Asn Thr Thr Gln Leu Phe Asn
                340                 345                 350

Asn Thr Tyr Ser Asn Gly Thr Ile Thr Leu Pro Cys Lys Ile Lys Gln
            355                 360                 365

Ile Ile Asn Met Trp Gln Gly Val Gly Gln Ala Met Tyr Ala Pro Pro
    370                 375                 380

Ile Ser Gly Arg Ile Asn Cys Leu Ser Asn Ile Thr Gly Leu Leu Leu
385                 390                 395                 400

Thr Arg Asp Gly Asn Asn Gly Thr Asn Glu Thr Phe Arg Pro Gly Gly
                405                 410                 415

Gly Asn Ile Lys Asp Asn Trp Arg Ser Glu Leu Tyr Lys Cys Lys Val
            420                 425                 430

Val Gln Ile Glu Pro Leu Gly Ile Ala Pro Thr Arg Ala Lys Arg Arg
    435                 440                 445

Val Val Glu Arg Glu Lys Lys
    450                 455

<210> SEQ ID NO 19
<211> LENGTH: 354
<212> TYPE: PRT
<213> ORGANISM: Human herpesvirus

<400> SEQUENCE: 19

Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
                20                  25                  30

Asn Ser Ser Leu Thr Ser Ile Leu Ile Pro Met Gln Asn Asp Asn Tyr
            35                  40                  45

Thr Glu Ile Lys Gly Gln Leu Val Phe Ile Gly Glu Gln Leu Pro Thr
        50                  55                  60

Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
```

```
                 85                  90                  95
Arg Ile Arg Thr Ser Ala Phe Ile Ser Cys Arg Tyr Lys His Ser Trp
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175

Val Ile Tyr Thr Ser Pro Ser Leu Gln Asn Gly Tyr Ser Thr Arg Ala
            180                 185                 190

Leu Phe Gln Gln Ala Arg Leu Cys Asp Leu Pro Ala Thr Pro Lys Gly
        195                 200                 205

Ser Gly Thr Ser Leu Phe Gln His Met Leu Asp Leu Arg Ala Gly Lys
    210                 215                 220

Ser Leu Glu Asp Asn Pro Trp Leu His Glu Asp Val Val Thr Thr Glu
225                 230                 235                 240

Thr Lys Ser Val Val Lys Glu Gly Ile Glu Asn His Val Tyr Pro Thr
                245                 250                 255

Asp Met Ser Thr Leu Pro Glu Lys Ser Leu Asn Asp Pro Pro Glu Asn
            260                 265                 270

Leu Leu Ile Ile Ile Pro Ile Val Ala Ser Val Met Ile Leu Thr Ala
        275                 280                 285

Met Val Ile Val Ile Val Ile Ser Val Lys Arg Arg Arg Ile Lys Lys
    290                 295                 300

His Pro Ile Tyr Arg Pro Asn Thr Lys Thr Arg Arg Gly Ile Gln Asn
305                 310                 315                 320

Ala Thr Pro Glu Ser Asp Val Met Leu Glu Ala Ala Ile Ala Gln Leu
                325                 330                 335

Ala Thr Ile Arg Glu Glu Ser Pro Pro His Ser Val Val Asn Pro Phe
            340                 345                 350

Val Lys

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Asp Leu Gln Val Leu
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Val Pro Asp Tyr Ala
1               5
```

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Pro Tyr Asp Val Pro Asp Tyr Ala Ser Leu Arg Ser
1               5                   10

<210> SEQ ID NO 23
<211> LENGTH: 17
<212> TYPE: PRT
<213> ORGANISM: Homo sapiens

<400> SEQUENCE: 23

Glu Asn Pro Val Val His Glu Phe Lys Asn Ile Val Thr Pro Arg Thr
1               5                   10                  15

Pro

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Lys Pro Val Val His Leu Phe Ala Asn Ile Val Thr Pro Arg Thr
1               5                   10                  15

Pro

<210> SEQ ID NO 25
<211> LENGTH: 13
<212> TYPE: PRT
<213> ORGANISM: Homo sapiens

<400> SEQUENCE: 25

Ala Lys Ala Val Ala Ala Trp Thr Leu Lys Ala Ala Ala
1               5                   10

<210> SEQ ID NO 26
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Ala
<220> FEATURE:
<221> NAME/KEY: MOD_RES
<222> LOCATION: (3)..(3)
<223> OTHER INFORMATION: Ile or Ala
<220> FEATURE:
<221> NAME/KEY: MOD_RES
<222> LOCATION: (4)..(4)
<223> OTHER INFORMATION: Pro or Ala
<220> FEATURE:
<221> NAME/KEY: MOD_RES
<222> LOCATION: (5)..(5)
<223> OTHER INFORMATION: Lys or Ala -continued

```
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MOD_RES
<222> LOCATION: (7)..(7)
<223> OTHER INFORMATION: Ser or Ala
<220> FEATURE:
<221> NAME/KEY: MOD_RES
<222> LOCATION: (8)..(8)
<223> OTHER INFORMATION: Trp or Ala
<220> FEATURE:
<221> NAME/KEY: MOD_RES
<222> LOCATION: (9)..(9)
<223> OTHER INFORMATION: Ser, Pro or Ala
<220> FEATURE:
<221> NAME/KEY: MOD_RES
<222> LOCATION: (10)..(10)
<223> OTHER INFORMATION: Asp, Ser, Asn or Ala
<220> FEATURE:
<221> NAME/KEY: MOD_RES
<222> LOCATION: (11)..(11)
<223> OTHER INFORMATION: His or Ala
<220> FEATURE:
<221> NAME/KEY: MOD_RES
<222> LOCATION: (12)..(12)
<223> OTHER INFORMATION: Glu, Asp or Ala
<220> FEATURE:
<221> NAME/KEY: MOD_RES
<222> LOCATION: (14)..(14)
<223> OTHER INFORMATION: Ser or Ala
<220> FEATURE:
<221> NAME/KEY: MOD_RES
<222> LOCATION: (15)..(15)
<223> OTHER INFORMATION: Ser, Leu or Ala
<220> FEATURE:
<221> NAME/KEY: MOD_RES
<222> LOCATION: (19)..(19)
<223> OTHER INFORMATION: Ser or Ala
<220> FEATURE:
<221> NAME/KEY: MOD_RES
<222> LOCATION: (21)..(21)
<223> OTHER INFORMATION: Cys or Ala
<220> FEATURE:
<221> NAME/KEY: MOD_RES
<222> LOCATION: (24)..(24)
<223> OTHER INFORMATION: Gln, His, Asn, Leu or Ala
<220> FEATURE:
<221> NAME/KEY: MOD_RES
<222> LOCATION: (25)..(25)
<223> OTHER INFORMATION: Gly or Ala
<220> FEATURE:
<221> NAME/KEY: MOD_RES
<222> LOCATION: (26)..(26)
<223> OTHER INFORMATION: Arg, Lys, Ser, Val, Thr, Gly or Ala
<220> FEATURE:
<221> NAME/KEY: MOD_RES
<222> LOCATION: (27)..(27)
<223> OTHER INFORMATION: Ser, Pro or Ala
<220> FEATURE:
<221> NAME/KEY: MOD_RES
<222> LOCATION: (30)..(30)
<223> OTHER INFORMATION: Phe or Tyr
<220> FEATURE:
<221> NAME/KEY: MOD_RES
<222> LOCATION: (37)..(37)
<223> OTHER INFORMATION: Ile, Thr, Val or Ala
<220> FEATURE:
<221> NAME/KEY: MOD_RES
<222> LOCATION: (38)..(38)
<223> OTHER INFORMATION: Lys, Thr, Glu or Ala
<220> FEATURE:
<221> NAME/KEY: MOD_RES
<222> LOCATION: (39)..(39)
<223> OTHER INFORMATION: Lys, Arg or Ala
<220> FEATURE:
<221> NAME/KEY: MOD_RES
<222> LOCATION: (40)..(40)
```

```
<223> OTHER INFORMATION: Asp, Asn or Ala
<220> FEATURE:
<221> NAME/KEY: MOD_RES
<222> LOCATION: (41)..(41)
<223> OTHER INFORMATION: Asn, Ser, Asp or Ala
<220> FEATURE:
<221> NAME/KEY: MOD_RES
<222> LOCATION: (42)..(42)
<223> OTHER INFORMATION: Ala, Thr or Ser
<220> FEATURE:
<221> NAME/KEY: MOD_RES
<222> LOCATION: (48)..(48)
<223> OTHER INFORMATION: Arg or Lys

<400> SEQUENCE: 26

Cys Xaa Xaa Xaa Xaa Xaa Xaa Xaa Xaa Xaa Xaa Xaa Ala Xaa Xaa Gly
1               5                   10                  15

Val Ser Xaa Ala Xaa Pro Tyr Xaa Xaa Xaa Xaa Ser Phe Xaa Arg Asn
            20                  25                  30

Val Val Trp Leu Xaa Xaa Xaa Xaa Xaa Xaa Tyr Pro Thr Ile Lys Xaa
        35                  40                  45

Ser Tyr Cys
    50
```